(12) United States Patent
Shepard et al.

(10) Patent No.: US 6,598,276 B2
(45) Date of Patent: Jul. 29, 2003

(54) FASTENER LOOP MATERIAL, ITS MANUFACTURE, AND PRODUCTS INCORPORATING THE MATERIAL

(75) Inventors: William H. Shepard, Amherst, NH (US); Paul R. Erickson, New Boston, NH (US)

(73) Assignee: Velcro Industries B.V., Curacao (AN)

(*) Notice: Subject to any disclaimer, the term of this patent is extended or adjusted under 35 U.S.C. 154(b) by 0 days.

(21) Appl. No.: 09/989,784

(22) Filed: Nov. 20, 2001

(65) Prior Publication Data

US 2002/0029441 A1 Mar. 14, 2002

Related U.S. Application Data

(63) Continuation of application No. 08/922,292, filed on Sep. 3, 1997, now Pat. No. 6,342,285.

(51) Int. Cl.[7] ............................ D06C 3/00; D04H 3/10; D04H 11/08; B32B 5/14

(52) U.S. Cl. .............................. 26/51; 28/103; 28/104; 28/107; 28/161; 28/159; 26/2 R; 427/171; 427/176

(58) Field of Search ........................... 28/104, 107, 111, 28/112, 159, 161, 162; 24/442, 445, 446, 447, 448; 26/2 R, 51, 52, 53; 427/171, 172, 173, 176

(56) References Cited

U.S. PATENT DOCUMENTS

| | | |
|---|---|---|
| 2,913,803 A | 11/1959 | Dodds |
| 3,152,381 A | 10/1964 | Priester, Jr. et al. |
| 3,341,386 A | 9/1967 | White et al. |
| 3,347,735 A | 10/1967 | Dildilian |
| 3,674,618 A | 7/1972 | Spann |
| 3,694,867 A | 10/1972 | Stumpf |
| 3,705,065 A | 12/1972 | Stumpf |
| 3,708,361 A | 1/1973 | Stumpf |
| 3,708,833 A | 1/1973 | Ribich et al. .................. 24/204 |

(List continued on next page.)

FOREIGN PATENT DOCUMENTS

| | | |
|---|---|---|
| EP | 0 482 749 A1 | 4/1992 |
| EP | 0 605 013 A1 | 6/1994 |
| EP | 0 604 731 A1 | 7/1994 |
| EP | 0 765 616 A1 | 2/1997 |
| EP | 0 780 505 A2 | 6/1997 |
| EP | 0 341 993 | 11/1998 |
| EP | 0 937 420 A2 | 8/1999 |
| GB | 2 285 093 A | 6/1995 |
| GB | 2 290 052 | 12/1995 |

(List continued on next page.)

OTHER PUBLICATIONS

Principles of Polymer Systems, 2nd ed., F. Rodriguez; Table A5.2, p. 538.*
Assoc. of the Nonwoven Fabrics Industry, "The Needlepunch Primer", Inda pp. 1–29 (1995).
Foster, "Needlepunhcing a Unique Sector," FW: Nonwovens Manufacturing, pp. 2–6 (1996).

*Primary Examiner*—Cheryl A. Juska
(74) *Attorney, Agent, or Firm*—Fish & Richardson P.C.

(57) ABSTRACT

Lightweight, non-woven loop products for hook-and-loop fastening are disclosed, as are methods for making them and end products employing them. The products are non-woven webs of entangled fibers of substantial tenacity, the fibers forming both a sheet-form, bonded web body and hook-engageable, free-standing loops extending from the web body. The product is, in important cases, stretched before bonding to produce spaced-apart loop clusters extending from a very thin web of taut fibers. In important cases a binder is added to stabilize the product in its stretched condition. An example of the loop product is produced by needle-punching a batt of staple fibers in multiple needle-punching operations, applying a foamed acrylic binder, and then stretching the needled batt and curing the binder with the batt stretched. Other forming techniques are disclosed and several novel articles employing such loop products are described.

40 Claims, 17 Drawing Sheets

U.S. PATENT DOCUMENTS

| | | | |
|---|---|---|---|
| 3,720,578 A | 3/1973 | Heling et al. | |
| 3,756,907 A | 9/1973 | Heling | |
| 3,822,162 A | 7/1974 | Stumpf | |
| 4,116,892 A | 9/1978 | Schwarz | |
| 4,154,885 A | 5/1979 | Tecl et al. | |
| 4,154,889 A | 5/1979 | Platt | |
| 4,223,059 A | 9/1980 | Schwarz | |
| 4,258,097 A | 3/1981 | Benedyk | 428/224 |
| 4,295,251 A | 10/1981 | Tatham et al. | |
| 4,320,167 A | 3/1982 | Wishman | 428/89 |
| 4,363,845 A | 12/1982 | Hartmann | |
| 4,377,889 A | 3/1983 | Tatham et al. | |
| 4,379,189 A | 4/1983 | Platt | |
| 4,389,442 A | 6/1983 | Pickens, Jr. et al. | |
| 4,391,866 A | 7/1983 | Pickens, Jr. et al. | |
| 4,418,104 A | 11/1983 | Kiyomura et al. | |
| 4,424,250 A | 1/1984 | Adams et al. | 428/198 |
| 4,446,189 A | 5/1984 | Romanek | |
| 4,451,314 A | 5/1984 | Knoke et al. | |
| 4,451,315 A | 5/1984 | Miyazaki | |
| 4,490,425 A | 12/1984 | Knoke et al. | |
| 4,536,439 A | 8/1985 | Forsten | |
| 4,600,605 A | 7/1986 | Nakai et al. | |
| 4,600,618 A | 7/1986 | Raychok, Jr. et al. | 428/92 |
| 4,624,116 A | 11/1986 | Rogers | 66/193 |
| 4,645,699 A | 2/1987 | Neveu | 428/95 |
| 4,654,246 A | 3/1987 | Provost et al. | 428/88 |
| 4,739,635 A | 4/1988 | Conley et al. | 66/190 |
| 4,750,443 A | 6/1988 | Blaustein et al. | |
| 4,761,318 A | 8/1988 | Ott et al. | 428/85 |
| 4,806,300 A | 2/1989 | Walton et al. | |
| 4,931,343 A | 6/1990 | Becker et al. | 428/95 |
| 4,973,326 A | 11/1990 | Wood et al. | 604/391 |
| 4,981,749 A | 1/1991 | Kubo et al. | 428/129 |
| 4,992,124 A | 2/1991 | Kurihara et al. | |
| 5,032,122 A | 7/1991 | Noel et al. | 604/391 |
| 5,066,289 A | 11/1991 | Polski | |
| 5,144,730 A | 9/1992 | Dilo | |
| 5,151,320 A | 9/1992 | Homonoff et al. | |
| 5,214,942 A | 6/1993 | Peake, III et al. | 66/194 |
| 5,216,790 A | 6/1993 | Eschenbach | |
| 5,256,231 A | 10/1993 | Gorman et al. | |
| 5,267,453 A | 12/1993 | Peake, III et al. | 66/194 |
| 5,304,162 A | 4/1994 | Kuen | 604/391 |
| 5,326,612 A | 7/1994 | Goulait | |
| 5,380,313 A | 1/1995 | Goulait et al. | 604/391 |
| 5,382,461 A | 1/1995 | Wu | 428/86 |
| 5,383,872 A | 1/1995 | Roessler et al. | 604/391 |
| 5,386,595 A | 2/1995 | Kuen et al. | 2/400 |
| 5,391,424 A | 2/1995 | Kolzer | 428/220 |
| 5,403,302 A | 4/1995 | Roessler et al. | |
| 5,407,439 A | 4/1995 | Goulait | 604/391 |
| 5,407,722 A | 4/1995 | Peake, III et al. | 428/88 |
| 5,423,789 A | 6/1995 | Kuen | |
| 5,447,590 A | 9/1995 | Gilpatrick | 156/178 |
| 5,449,530 A | 9/1995 | Peake, III et al. | 427/244 |
| 5,470,417 A | 11/1995 | Goulait | 156/201 |
| 5,476,702 A | 12/1995 | Datta et al. | 428/99 |
| 5,500,268 A | 3/1996 | Billarant | 428/100 |
| 5,518,795 A | 5/1996 | Kennedy et al. | 428/100 |
| 5,531,732 A | 7/1996 | Wood | |
| 5,542,942 A | 8/1996 | Kline et al. | |
| 5,547,531 A | 8/1996 | Allen et al. | |
| 5,554,239 A | 9/1996 | Datta et al. | |
| 5,565,255 A | 10/1996 | Young et al. | |
| 5,569,233 A | 10/1996 | Goulait | |
| 5,586,371 A | 12/1996 | Thomas | |
| 5,595,567 A | 1/1997 | King et al. | |
| 5,605,729 A | 2/1997 | Mody et al. | 428/37 |
| 5,611,791 A | 3/1997 | Gorman et al. | |
| 5,614,232 A | 3/1997 | Torigoe et al. | |
| 5,614,281 A | 3/1997 | Jackson et al. | |
| 5,615,460 A | 4/1997 | Weirich et al. | |
| 5,616,155 A | 4/1997 | Kronzer | 51/295 |
| 5,616,394 A | 4/1997 | Gorman et al. | |
| 5,618,583 A | 4/1997 | Young et al. | |
| 5,620,779 A | 4/1997 | Levy et al. | |
| 5,622,578 A | 4/1997 | Thomas | |
| 5,624,427 A | 4/1997 | Bergman et al. | |
| 5,647,864 A | 7/1997 | Allen et al. | |
| 5,654,070 A | 8/1997 | Billarant | 428/100 |
| 5,664,302 A | 9/1997 | Thomas | |
| 5,669,900 A | 9/1997 | Bullwinkel et al. | 604/391 |
| 5,669,901 A | 9/1997 | LaFortune et al. | 604/391 |
| 5,685,756 A | 11/1997 | Noda | |
| 5,695,377 A | 12/1997 | Triebes et al. | |
| 5,699,593 A | 12/1997 | Jackson | |
| 5,707,707 A | 1/1998 | Burnes et al. | 428/95 |
| 5,722,968 A | 3/1998 | Datta et al. | 604/391 |
| 5,736,214 A | 4/1998 | Billarant | |
| 5,747,584 A | 5/1998 | Noda | |
| 5,773,120 A | 6/1998 | Deka et al. | |
| 5,843,057 A | 12/1998 | McCormack | |
| 5,858,515 A | 1/1999 | Stokes et al. | |

FOREIGN PATENT DOCUMENTS

| | | |
|---|---|---|
| JP | 2-41156 | 2/1990 |
| JP | 2-191735 | 7/1990 |
| JP | 4-56008 | 5/1992 |
| JP | 6-33359 | 2/1994 |
| JP | 6-123061 | 5/1994 |
| JP | 6-141913 | 5/1994 |
| JP | 07300752 A | 11/1994 |
| JP | 7-231842 | 5/1995 |
| JP | 71-71011 | 11/1995 |
| JP | 8-27657 | 1/1996 |
| JP | 9-195153 | 7/1997 |
| JP | 9-195154 | 7/1997 |
| JP | 9-195155 | 7/1997 |
| JP | 9-309168 | 12/1997 |
| JP | 10-146207 | 6/1998 |
| JP | 10-151005 | 6/1998 |
| JP | 10-165207 | 6/1998 |
| JP | 10-259560 | 9/1998 |
| WO | WO 92/01401 | 2/1992 |
| WO | WO 95/17111 | 6/1995 |
| WO | WO 96/03101 | 2/1996 |
| WO | WO 96/14459 | 5/1996 |
| WO | WO 98/33410 | 8/1998 |

\* cited by examiner

FASTENER LOOP MATERIAL, ITS MANUFACTURE, AND PRODUCTS INCORPORATING THE MATERIAL

This application is a continuation of U.S. application Ser. No. 08/922,292, filed Sep. 3, 1997 now U.S. Pat. No. 6,342,285. The disclosure of the prior application is considered part of(and is incorporated by reference) the disclosure of this application.

BACKGROUND OF THE INVENTION

This application is a continuation of U.S. application Ser. No. 08/922,292, filed Sep. 3, 1997, now U.S. Pat. No 6,342,285. The disclosure of the prior application is considered part of (and is incorporated by reference in) the disclosure of this application.

This invention relates to loop material, particularly to material to be engaged with hooking members to form a fastening, and to its manufacture and use.

In the production of woven and non-woven materials, it is common to form the material as a-continuous web that is subsequently spooled. In woven and knit loop materials, loop-forming filaments or yarns are included in the structure of a fabric to form upstanding loops for engaging hooks. As hook-and-loop fasteners find broader ranges of application, especially in inexpensive, disposable products, some forms of non-woven materials have been suggested to serve as a loop material to reduce the cost and weight of the loop product while providing adequate closure performance in terms of peel and shear strength. Nevertheless, cost of the loop component has remained a major factor limiting the extent of use of hook and loop fasteners.

SUMMARY OF THE INVENTION

We have realized that non-woven fabrics constructed with certain structural features are capable of functioning well for their intended purpose as hook-engageable loop fabrics, while providing particular advantage in regard to expense of manufacture and other properties.

According to one aspect of the invention, a loop product for hook-and-loop fastening is provided, the loop product comprising a non-woven, uncompressed and unshrunk web of entangled fibers of substantial tenacity and of uniform fiber composition, the fibers forming both a sheet-form, web body and hook-engageable, free-standing loops extending from the web body, the product having a basis weight of less than about 2 ounces per square yard. "Uniform fiber composition" as used here includes a loop-forming fiber blend that is uniform, i.e. not formed by layers of two different types.

Preferred products according to this aspect of the invention have one or more of the following features.

The loop product has an overall thickness, including the web body and a majority of the loops, of less than about 0.150 inch, in many instances preferably less than about 0.100 inch.

The loops extend from associated entanglements within the main web body to an average loop height, measured as the perpendicular distance from the web body, from their associated entanglements, of between about 0.020 and 0.060 inch, preferably, in many instances the average loop height being between about 0.5 and 0.6 times the overall thickness of the product.

Another aspect of the invention, is a hook-engageable loop fabric if basis weight less than 4 ounces per square yard having all of the above features, but without regard to whether the fabric is made of fibers of uniform composition.

In either case, in preferred embodiments, the web body is stabilized in a stretched condition, the web body including knots formed by tightened fiber entanglements.

In preferred cases of each of these aspects of the invention, the web body is stabilized in a condition of at least 20 percent areal stretch, and in certain of these cases the web body is stabilized in a condition of at least 10 percent stretch in each of two perpendicular directions. In certain important cases the knot density is between about 50 and 1000 knots per square inch of web body.

Preferably the fibers generally have a tenacity of at least 2.8 grams per denier; in many instances the fibers generally have a tenacity of at least 5 grams per denier, and in certain important instances the fibers generally have a tenacity of at least 8 grams per denier.

The loops preferably extend from the web body to varied heights to form a multi-level arrangement of hook-engageable loops.

The web is preferably stabilized in a stretched condition, the web body including knots formed by tightened web entanglements, the loops extending from loop structures, at least some of the loop structures each comprising a common, elongated trunk portion extending from the web from an associated knot, and multiple loops extend from the trunk portion.

The fibers are preferably of a material selected from the group consisting of polyester, polyurethane, polypropylene, polyethylene and nylon, homopolymers, mixtures, copolymers, alloys, or coextrusions thereof, and natural fibers. In certain presently preferred cases the fibers are polyester.

The loop product preferably has a Gurley stiffness of less than about 300 milligrams.

The loop product preferably comprises a binder selected from the group consisting of acrylics, urethanes, polyvinyls, formaldehydes, glyoxals and epoxies.

In other cases the loop product preferably comprises polymer filaments entangled among fibers of substantial tenacity the filaments being at least partially melted to bond the web body.

According to another aspect of the invention, a non-woven loop fabric for engaging hooks in a hook-and-loop fastener is provided, the fabric having a basis weight of less than about 2 ounces per square yard and comprising a stretched, non-woven mat of fibers entangled at knots therein, the mat having a front side and free-standing and spaced-apart loop structures extending at least from the front side of the mat from the knots in the mat, these structures defining hook-engageable loops and corresponding associated knots.

Preferred products according to this aspect have one or more of the following features.

The mat of the loop fabric is stabilized in a condition of at least about 20 percent areal stretch, in important instances the mat is stabilized in a condition of at least 50 percent areal stretch, and in many instances preferably the mat is stabilized in a condition of at least 100 percent areal stretch. A presently preferred range is 75 percent to 150 percent.

The mat is stabilized in a condition of at least 10 percent stretch in each of two perpendicular directions, in many instances the mat is stabilized in a condition of at least 25 percent stretch in each of two perpendicular directions.

At least some of the knots of the mat are secured to resist relative fiber motion and further stretching of the fabric, preferably the loop fabric further comprising a binder to secure the fibers of the loop structures at their associated knots, in many instances the loop fabric comprising between about 20 and 40 percent binder, by weight, in many preferred instances the fabric being about one third by weight of binder.

In preferred cases the binder is selected from the group consisting of acrylics, urethanes, polyvinyls, formaldehydes, glyoxals and epoxies. In other cases the binder comprises polymer filaments entangled among the fibers, the filaments being at least partially melted to encapsulate the knots, and set. In certain cases the binder forms a backing adapted to be welded to a substrate, and in certain cases the binder forms an impermeable barrier. In certain cases the binder comprises a fire-retardant material.

At least some of the loop structures of the loop fabric each comprise multiple loops emanating from a common fiber knot.

Similarly to the first mentioned aspects of the invention, in implementations of the present aspect of the present invention the loop fabric preferably has an overall thickness, including the mat and a majority of the loop structures, of less than about 0.150 inch.

Likewise, the loop fabric preferably has loops that extend to an average loop height from their associated entanglements, measured as the perpendicular distance from the mat, of between about 0.020 and 0.060 inch and, preferably in many instances the average loop height is between about 0.5 and 0.6 times the overall thickness of the fabric.

In preferred cases, the knot density of the loop fabric is between about 50 and 1000 knots per square inch of mat, in certain preferred cases the knot density being between about 100 and 600 knots per square inch of mat, and in particularly important cases the knot density being between about 150 and 300 knots per square inch of mat.

In preferred cases, the fibers generally have a tenacity of at least 2.8 grams per denier, in particular cases the fibers generally have a tenacity of at least 5 grams per denier and in other cases the fibers generally have a tenacity of at least 8 grams per denier.

In preferred cases the loops of the loop structures extend from the mat to varied heights to form a multi-level arrangement of hook-engageable loops.

In preferred cases at least some of the loop structures each comprise a common, elongated trunk portion extending from the mat from an associated knot and multiple loops extend from the trunk portion.

Also in preferred cases the loop structures generally each comprise three or more hook-engageable loops.

In preferred cases the fibers are generally of 15 denier or less; while in particular cases the fibers are generally of 8 denier or less.

In important implementations of this aspect of the invention the fibers are crimped at a crimp density of at least about 7 crimps per inch, the fibers are of a material selected from the group consisting of polyester, polyurethane, polypropylene, polyethylene, nylon, and homopolymers, mixtures, copolymers, alloys, and coextrusions thereof and natural fibers and the loop fabric has a Gurley stiffness of less than about 300 milligrams; in important cases the loop fabric has a Gurley stiffness of less than about 100 milligrams.

According to another aspect of the invention a loop product for hook-and-loop fastening is provided, comprising a stretched, non-woven fabric of entangled fibers having front and back surfaces, the front surface having exposed, through-forced loops of the fibers extending therefrom, capable of being engaged by hook-type fasteners, and a binder securing the fibers at the back surface of the fabric to resist further elongation of the fabric.

According to another aspect of the invention a loop product for hook-and-loop fastening is provided, comprising a stretched, non-woven fabric of entangled fibers having front and back surfaces, the front and back surfaces having exposed, through-forced loops of said fiber extending therefrom, capable of being engaged by hook-type fasteners, and a binder securing the fibers to resist further elongation of the fabric.

According to another aspect of the invention a hook-and-loop fastener is provided, comprising a loop product according to any of the preceding aspects of the invention, preferably with one or more of the further described features, and a hook portion preferably of molded construction, having an array of hooking elements extending from a sheet-form base, the hooking elements constructed to engage the hook-engageable loops of the loop product to form a releasable fastening.

In preferred cases of this aspect the hook-and-loop fastener has an overall thickness, engaged and at rest, of about 0.075 inch or less, and in certain preferred cases the hook-and-loop fastener has an overall thickness, engaged and at rest, of about 0.050 inch or less.

According to another aspect of the invention a substrate is provided comprising a surface layer of thermoplastic material and the loop product accordingly to any of the above-mentioned aspects, preferably with one or more of the further described features, at least some of the fibers of the fabric of the loop product opposite the hook-engageable loops being encapsulated within the layer of thermoplastic material, for instance by use of the techniques described in U.S. Pat. No. 5,518,795, which is hereby incorporated by reference as if it were fully set forth herein.

Another aspect of the invention is a package comprising a first closure portion comprising the loop product of any of the above mentioned aspects of the invention and a second closure portion having a hook product, preferably of molded plastic form, comprising an array of hooking elements extending from a sheet-form base, the hooking elements constructed to engage the extended loops of the loop product to hold the package in a closed or open position.

In preferred cases the loop product and the hook product of the package have a combined overall thickness, engaged and at rest, of less than about 0.075 inch.

Another aspect of the invention is a disposable article of clothing comprising the loop product of any of the above described aspects and features arranged to extensively cover a portion of a wearer's body or presented on a panel or tab that has been secured to the article of clothing as by pressure sensitive adhesive, and a fastener with hooking elements arranged to engage the loops of the fabric, panel or tab to form a releasable fastening to retain the article of clothing on a wearer.

In preferred cases, the disposable article of clothing comprises a surgical gown, in other cases a diaper and in these or other cases the fabric comprises a binder forming a water-resistant or water impermeable liner.

In still another product aspect of the invention an air filter is provided comprising the loop product of any of the foregoing aspects and preferred features constructed to be mounted and act to intercept and filter a flow of air.

By "hook-engageable" and similar terms used above and throughout this specification, we mean that the loop material defines openings of size adequate to receive the tip or head portion of a male fastener element (such as a hook-shape or mushroom-shape element, for instance) for forming a fastening.

By the word "entanglements" we mean the nodes at which a multiplicity of fibers are intertwined in the non-woven web. These entanglements may be relatively loose, as formed directly by a needling process, for instance, or tightened after formation of the entanglements. By the word "knots" we mean entanglements that have been tightened by applying tension to their intertwined fibers in at least one direction in the plane of the web, and remain in an at least partially tightened state.

We have also realized that such loop fabrics as just described are advantageously produced by employing certain manufacturing techniques and methods.

An important aspect of the invention is a method of forming a loop product for a hook-and-loop fastener, the method comprising the steps of forming a batt of loose, staple fibers, entangling the fibers to produce a non-woven fabric of fibers joined at entanglements, with loops of some of the fibers extending from at least one side of the fabric, subsequently stretching the fabric to tighten the entanglements to form knots, and binding the knots to hold the fabric in its stretched state.

Another important aspect of the invention is a method of forming a loop product for a hook-and-loop fastener, the method comprising the steps of forming a batt of loose, staple fibers; forcing some of said fibers through the batt, thereby entangling the fibers to produce a non-woven fabric of fibers joined at entanglements, and also thereby forming fibrous loops extending from one side of the fabric, coating at least some of the entanglements of the fabric with a binder, and subsequently stretching the fabric to tighten the entanglements to form knots, the binder adapted to hold the fabric in its stretched state.

One or more of the following features can be employed to advantage with methods according to either of the aspects of the invention just described.

The batt is through-punched with needles.

The fibers are forced through the batt for entangling the fibers by needling the batt a first time with a needle-punching density of at least 100 punches per square inch, and needling the batt a second time with a greater needle-punching density. The batt is preferably needled a final time with a needle-punching density of between about 1200 and 1600 punches per square inch.

The batt is needled a first time in a first direction, and needled a subsequent time in a second direction, the second direction being opposite the first direction. In preferred cases, the batt is needled a first time and a second time in a first direction and needled a third time in the second direction.

The method includes setting a binder to stiffen the knots of the stretched fabric.

The fabric is stretched by at least 15 percent in a cross-machine direction.

The fabric is stretched to increase its area by at least about 20 percent, in certain preferred cases the fabric is stretched to increase its area by at least about 50 percent, and in particular cases the fabric is stretched to increase its area by at least about 100 percent.

The step of about stretching produces a fabric with a width of at least five feet, or even much more.

The method includes the step of brushing the loops to disentangle loosely-held loop fibers.

According to still another aspect of the invention a method of forming a loop component of a hook and loop fastener is provided comprising forming a stretchable non-woven fabric comprised of entangled fibers, some of the fibers forming hook-engageable loops that extend from the entanglements, thereafter stretching the thus formed web thereby tightening at least some of the entanglements into knots, and thereafter binding the stretched fabric to give it stability.

The invention can provide a very inexpensive loop product which can very effectively engage and retain hooks, such as in hook-and-loop fasteners. The loop product can be particularly useful in combination with extremely small, inexpensive molded hooks as fasteners for disposable products, such as diapers, medical devices or packaging.

DESCRIPTION OF EMBODIMENTS

Figure 1:
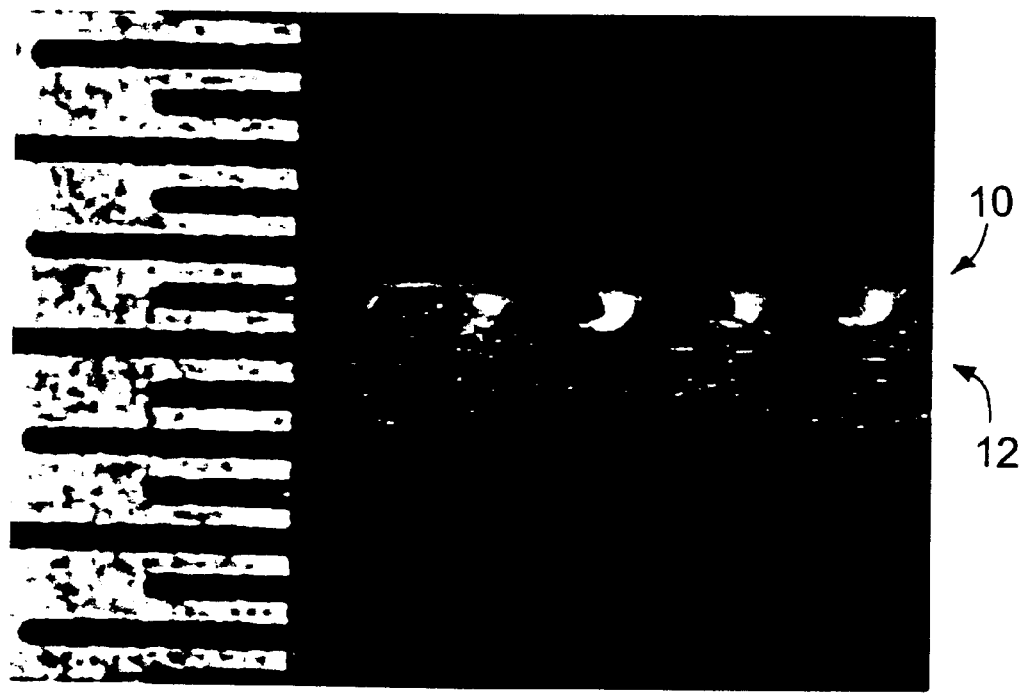
FIG. 1 is an enlarged side view of a hook-and-loop fastener, during disengagement.
Figure 2:
FIGS. 2 and 3 are enlarged plan and side views, respectively, of a loop fastener product.

Referring first to FIG. 1, a molded hook fastener product 10 is shown engaging the loops of a very thin loop product 12. The photograph is quite enlarged, as shown by the scale on the left side of the photograph. The minor divisions of the scale each represent a-length of 1/64th of an inch (0.0156 inch). Hook product 10 is of the CFM-29 designation, available from Velcro U.S.A. Inc. of Manchester, N.H., U.S.A., and has hooks of only 0.015 inch height. Referring also to FIG. 2, loop product 12, a feature of the present invention, is very thin (as evidenced by the scale of the photographs and its lack of opacity) and has relatively free fibers forming loops extending from one side of a continuous, tangled mat of fibers. In this and the following photographs all scale graduations, unless otherwise marked, are in 0.0156 inch (1/64 inch) increments.

As shown in FIG. 2, a substantial number of the fibers of the mat of loop product 12 are taut (i.e., not slack, regionally straight), extending between knots 18 of the loop product fabric. The taut fibers have been straightened by tension applied in at least one direction in the plane of the fabric mat. The individual fibers of the mat follow no definite pattern as in a woven product, but randomly lie in various directions within the plane of the fabric mat. The loops that extend from the loop product are of the same fibers that comprise the mat but extend beyond the general mass of the mat, usually from an associated knot 18. The knot density of the sample shown in the photograph was determined to be approximately 180 knots per square inch by counting the number of visible knots within a given square area. The knots themselves are fairly tight, made up of several monofilament fibers, and are interconnected by the taut fibers seen running between them. In between knots, the thin fiber mat is not very dense and is sheer enough to permit images to be readily seen through it. For low cost application, the fabric preferably weighs less than about 2 ounces or less per square yard.

In this particular embodiment, the fibers of the mat are held in their taut, straightened condition by a water-based, acrylic binder (not visible in the photograph) applied to the side of the mat opposite the loops to bind the mat fibers in their taut condition to stabilize the areal dimensions of the fabric, and-to secure the loops at their associated knots. The binder generally ranges between 20 and 40% of the total weight of the fabric and in the presently preferred embodiments accounts for about one third of the total product weight. The resulting fabric is dimensionally stable and strong enough to be suitable for further processing by standard fabric-handling techniques. The fabric also has a slight stiffness, like a starched felt, which can be mitigated by softeners or mechanical working if desired.

The individual fibers of loop fabric 12 shown in FIG. 2 have low denier and substantial tenacity (i.e., tensile strength per unit diameter) to work with very small hooks such as those illustrated in FIG. 1. Fibers with tenacity values of at least 2.8 grams per denier have been found to provide good closure performance, and fibers with tenacity of at least 5 or more grams per denier (preferably even 8 or more grams per denier) are even more preferred in many instances. In general terms for a loop-limited closure, the higher the loop tenacity, the stronger the closure. The fibers of fabric 12 of FIGS. 1 and 2 are 6 denier staple polyester fibers (cut to four inch lengths) and as a result of the method of the manufacture, are in a drawn, molecular oriented state, having been drawn with a draw ratio of at least 2:1 (i.e., to at least twice their original length) under cooling conditions that enable molecular orientation to occur, to provide a fiber tenacity of about 3.6 grams per denier. The fibers in this example are of round cross-section and are crimped at about 7.5 crimps per inch. Such fibers are available from E. I. Du Pont de Nemours & Co., Inc., in Wilmington, Del. under the designation T-3367 PE T-794W 6×4. The loop fiber denier should be chosen with the hook size in mind, with lower denier fibers typically selected for use with smaller hooks. For low-cycle applications for use with larger hooks (and therefore preferably larger diameter loop fibers), fibers of lower tenacity may be employed.

As an alternative to round cross-section fibers, fibers of other cross-sections having angular surface aspects, e.g. fibers of pentagon or pentalobal cross-section, can enhance knot tightening for certain applications. Regardless of the particular construction of the individual fibers, they are selected to have a surface character that permits slippage within the knot-forming entanglements during tightening so as to enable stretching the batt without undue fiber breakage.

Figure 3:
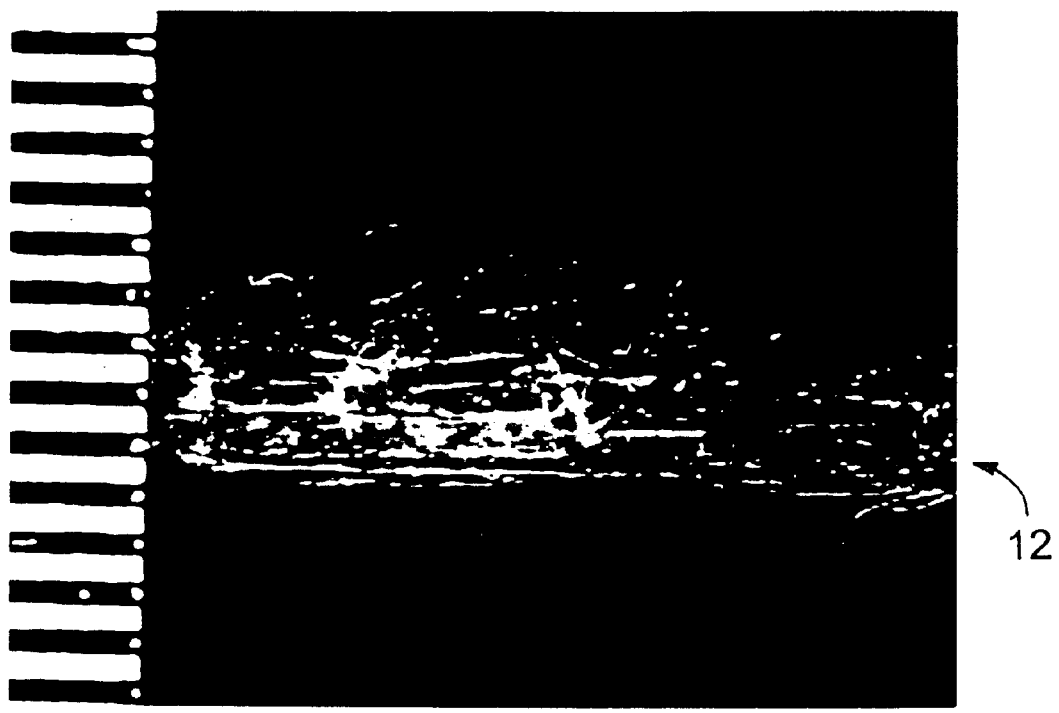
Figure 3A:
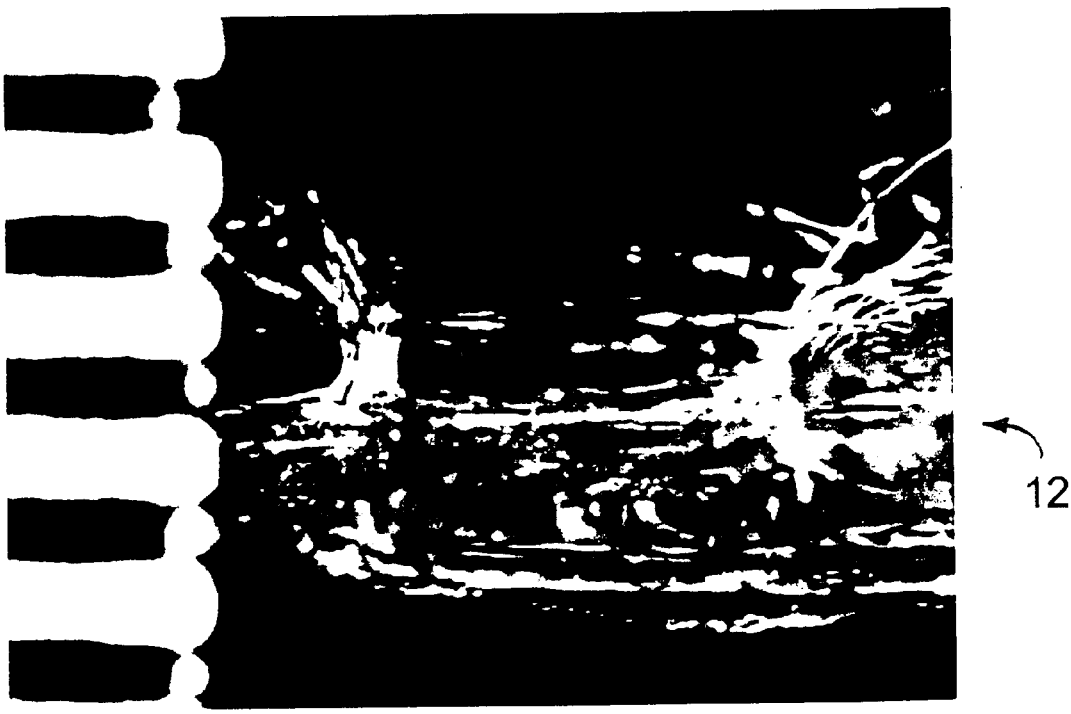
FIG. 3A is a further enlarged portion of the photograph of FIG. 3.
Figure 3B:
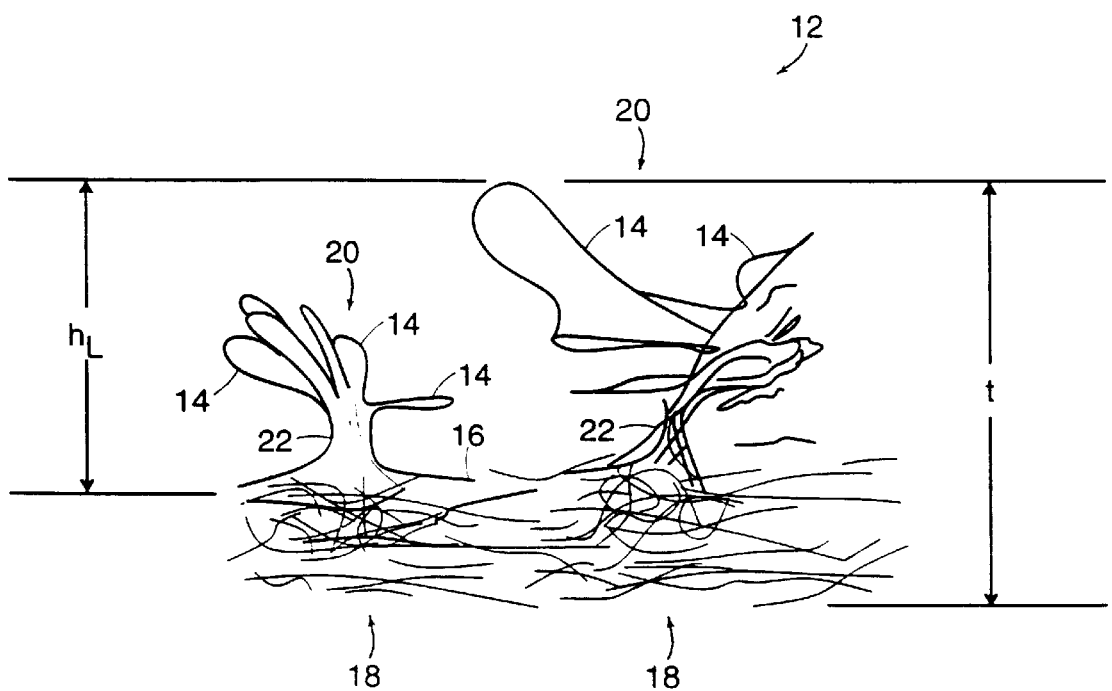
FIG. 3B is a sketch of the structure in the foreground of FIG. 3A.

Referring to FIGS. 3, 3A and 3B, the loops 14 of loop fabric 12 of this embodiment project primarily from one side of the fabric. The stabilizing binder, in this case, is applied to the other side. The loop product is extremely thin for use with very small hooks. The product shown, for instance, works well with hooks of about 0.015 inch height and has a loop height $h_L$ (i.e., the height of loops 14 from the near general surface of fiber mat 16) of about 0.055 inch. The loop product has an overall thickness, t, including a majority of the loops, of only about 0.090 inch. When measuring loop height in products without a visibly distinguishable upper mat surface, we define the near surface of the mat to be the lowest planar surface above about 80 percent of the total mass of fibers. The loops preferably vary in height for good engagement, and the average loop height should generally be greater than the height of the hooks with which the loop product is to be used, and preferably between 2 and 10 times the head height of the hooks used for applications requiring good shear strength. For fasteners which are-primarily loaded in peel, or by loads perpendicular to the plane of the base, the loops may be up to 15 times the head height of the hooks. For example, for use with 0.015 inch CFM-29 hooks (which have a head height of 0.006 inch), the average height $h_L$ of the loops should be between about 0.012 and 0.060 inch for good shear performance. For use with 0.097 inch CFM-24 hooks (which have a head height of 0.017 inch and are also available from Velcro U.S.A. Inc.), the average height of the loops should be at least 0.035 inch and may be as high as 0.250 inch for applications focusing on peel loading. For low cost, flexible loop fabrics, the average loop height should generally be between about 0.020 and 0.060 inch, and should be between about 0.5 and 0.6 times the overall thickness, t, of the loop product.

Figure 3C:
FIGS. 3C–3E are enlarged side views of other portions of the loop fastener product, showing various loop clusters.
Figure 3D:
Figure 3E:

As seen in FIGS. 3A and 3B, loops 14 extend from free-standing clusters of loop fibers extending from the fibrous mat 16. The clusters 20 which-have several monofilament loops 14 extending from a common elongated, substantially vertical trunk 22 we call "loop trees". Another example of a "loop tree" is seen in FIG. 3C. Other clusters 20' have one or more (typically several) extending loops but no elongated trunk. These clusters, examples of which can be seen in FIGS. 3D and 3E, we call "loop bushes". Each loop tree 20 or bush 20' extends from a corresponding knot 18 in which the loops of the cluster are anchored. Interstices between individual filaments in the trunk portion 22 of each tree or at the base of each bush, and in each knot 18 provide paths for the wicking of liquid binder, under the influence of surface tension-of the liquid binder, to provide additional localized stiffness and strength. Importantly, the density of clusters in the plan view is very low (FIG. 2), leaving sufficient room between the "branches" of neighboring bushes and trees to accommodate hooks and deflected loop material during engagement.

Figure 3F:
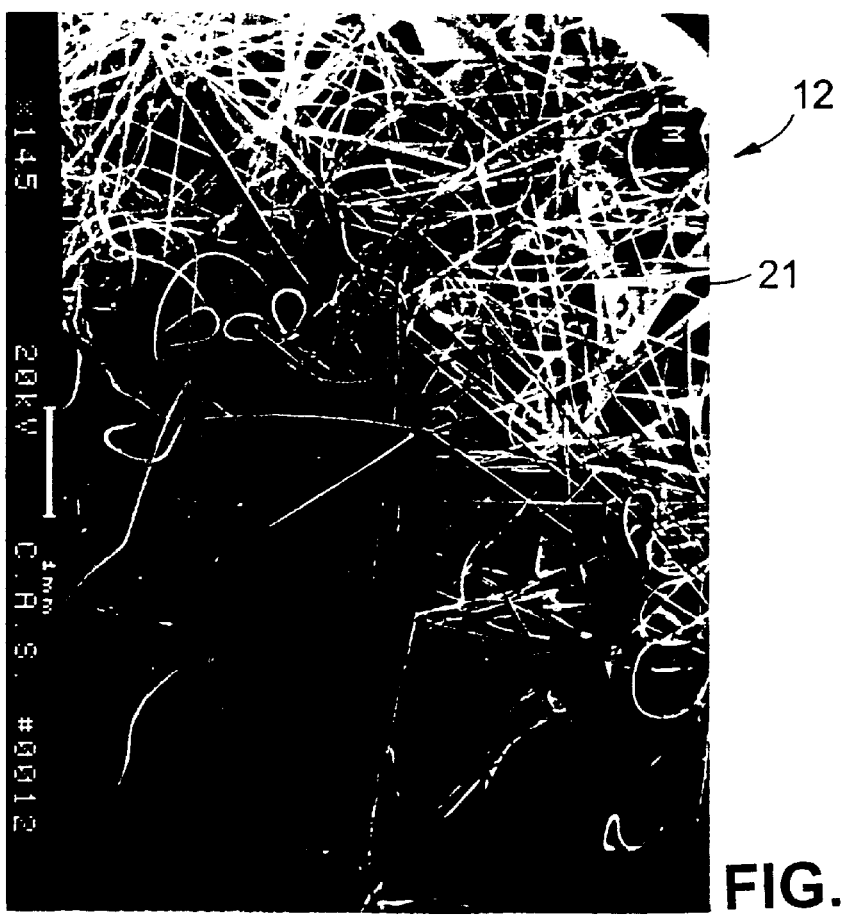
FIG. 3F is a highly enlarged plan view of a portion of the loop fastener product of FIG. 3.

Accumulations of solidified binder 21 can be seen in the knots in the highly magnified plan view of FIG. 3F. Applied in liquid form in this example, preferably before the knots are tightened, the binder contributes to securing the loops against being pulled out of the web.

Figure 11:
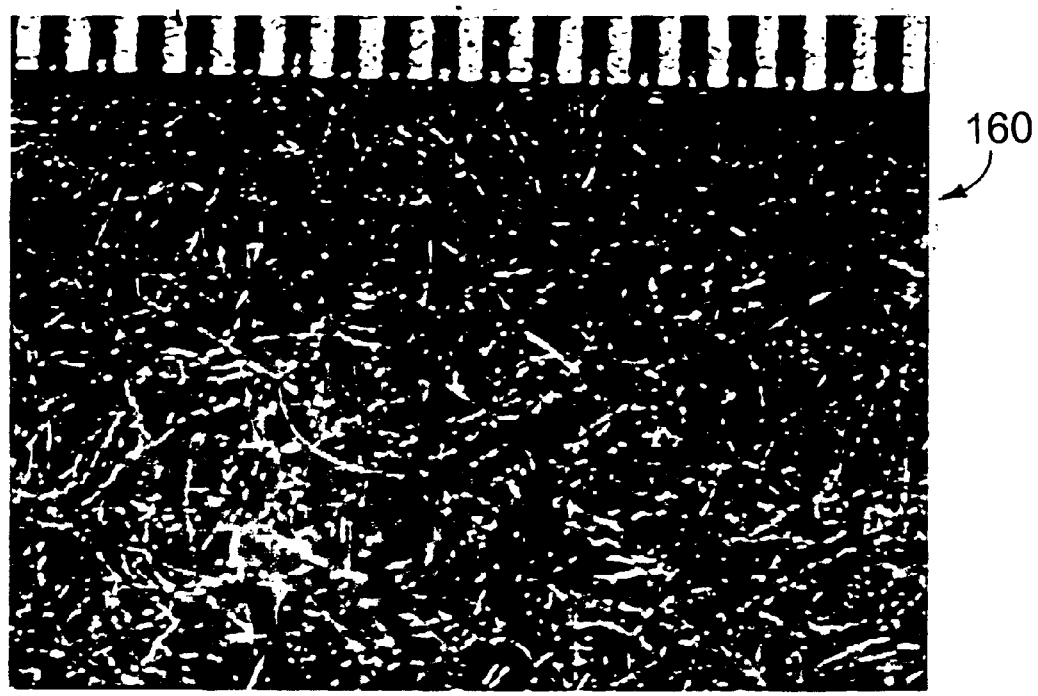
FIGS. 11 and 11A are plan and side views, respectively, of a batt of needled material after the second needling stage.
Figure 11A:
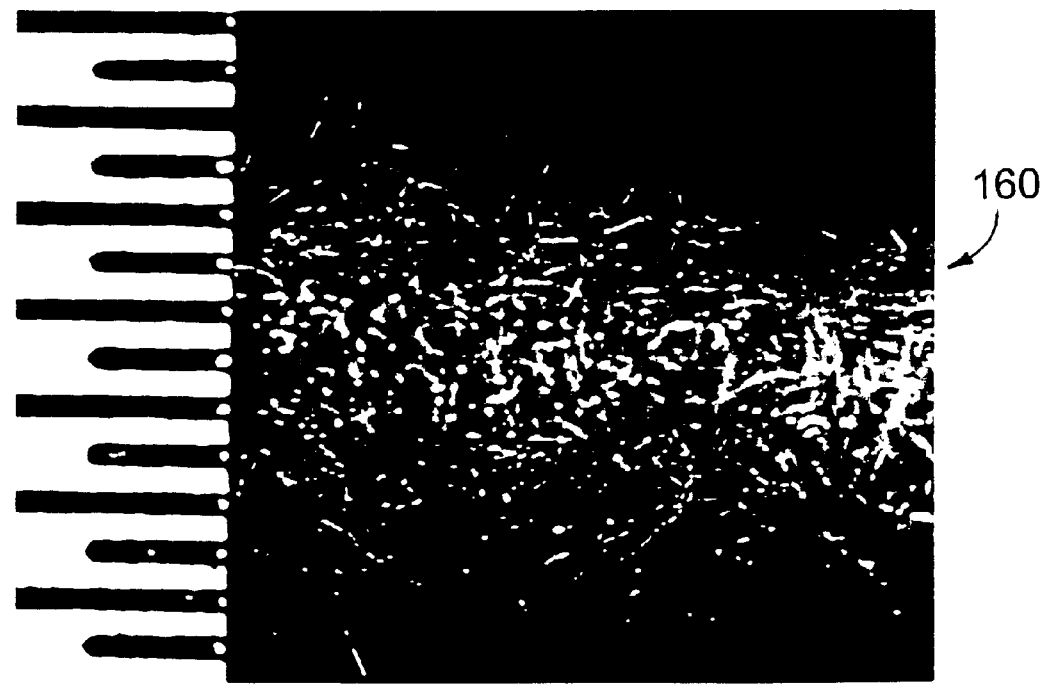

An unstretched product, as shown in FIGS. 11 and 11A for instance, may be used for engaging loops in applications requiring low closure strength and few closure cycles by suitably binding the loop-forming fibers within the main body of the web. In these cases the fabric, prior to application of binder weighs between 2 and 3 ounces per square yard, and the finished fabric weighs less than about 4 ounces per square yard. In such unstretched loop products, the gently arching loops and fibers of the web engaged by hooks are preferably bonded against being pulled from the web by application of a liquid binder, such as those discussed above. In important instances the web is treated under conditions that retain as much of its as-formed loop structure as possible during the bonding process, by avoiding compressing the upstanding loops in the direction of the thickness of the mat.

Figure 4:
FIG. 4 is an enlarged side view of the hook-and-loop fastener of FIG. 1, completely engaged.

Referring to FIG. 4, with proper clearance between loops for the accommodation of hooks, the fully engaged fastener (i.e., the loop product and mating hook product together) has an overall thickness of only the sum of the thickness of the hook product (including hooks) and the "ground" portion of the loop product (i.e., the thickness of the mat 16 between loop clusters, FIG. 3B). In other words, the free standing loops of the loop product do not add to the thickness of the completed fastener. Because of the ultra-thin ground portion 16 of the loop product disclosed herein (see FIG. 3B), the combination of loop product 12 with mating hook product 10 provides a fastening of very small thickness. For example, the engaged fastener of FIG. 4 has an overall thickness of only about 0.050 inch (thinner, in this case, than the overall thickness of the unengaged loop product, as the taller loop clusters are somewhat compressed by the hook product engaged with shorter loop clusters).

In addition to being advantageously thin, loop fabric formed according to the new principles is particularly flexible. Flexibility can be very important in some fastener applications, especially when the fastener must flex during use, as when used on an article of apparel. In such instances, the loop product of the invention should have a bending stiffness of less than about 300 milligrams, preferably less than about 100 milligrams, as measured with a Gurley type tester. More details on the use of Gurley type testers can be found in Method T 543 OM-94, published in 1984 by the Technical Association of Pulp and Paper (TAPPI).

Various synthetic or natural fibers may be employed in the invention. In some applications, wool and cotton may provide sufficient fiber strength. Presently, thermoplastic staple fibers which have substantial tenacity are preferred for making thin, low-cost loop product that has good closure performance when paired with very small molded hooks. For example, polyolefins (e.g., polypropylene or polyethylene), polyesters (e.g., polyethylene terephthalate), polyamides (e.g., nylon), acrylics and mixtures, alloys, copolymers and coextrusions thereof are suitable. Polyester is presently preferred.

Various binders may also be employed to stabilize the fabric. By "binder" we mean a material within the mat (other than the fibers forming the-main fastener loops) that secures the loop fibers at associated knots. In some applications, the binder is an adhesive. In other applications, the binder is in the form of fibers of low-melt polymer dispersed throughout and entangled within the fabric. These low-melt fibers are melted to wet the knot-forming entanglements and then cooled and solidified to secure the loops and stabilize the fabric. The binder preferably fully penetrates and permeates the interstices between individual fibers in the entanglements of the mat. When employing a liquid binder, the binder is preferably selected to have a sufficiently low viscosity and surface tension to enable it to flow into the untightened (or tightening) entanglements. In the embodiments in which the entanglements are subsequently tightened (such as the loop product shown in FIG. 2), this selected distribution of the fluid binder helps to secure the knots with minimal stiffening of the overall product and without requiring substantial amounts of binder.

In any event, the amount and penetration of the binder should be selected to avoid substantial interference with the desired hook-engaging function of the loops while adequately stabilizing the mat and securing the loops against being pulled from their associated entanglements. For use in applications in which the loop product may come in direct contact with sensitive skin, such as in diapers, the amount and type of binder should also be selected to be biocompatible to avoid skin irritation. As irritation can be aggravated by stiffness, preferably only enough binder to perform the above functions is applied. In some applications, for instance those in which the loop product is directly adhered to a supporting fabric and which does not require substantial fastener strength, the loop product may be provided without a binder.

In important instances, the binder also includes an organic or inorganic fire-retardant, such as antimony oxide, zinc borate, aluminum trihydrate or decabromobiphenyl oxide.

Figure 5A:
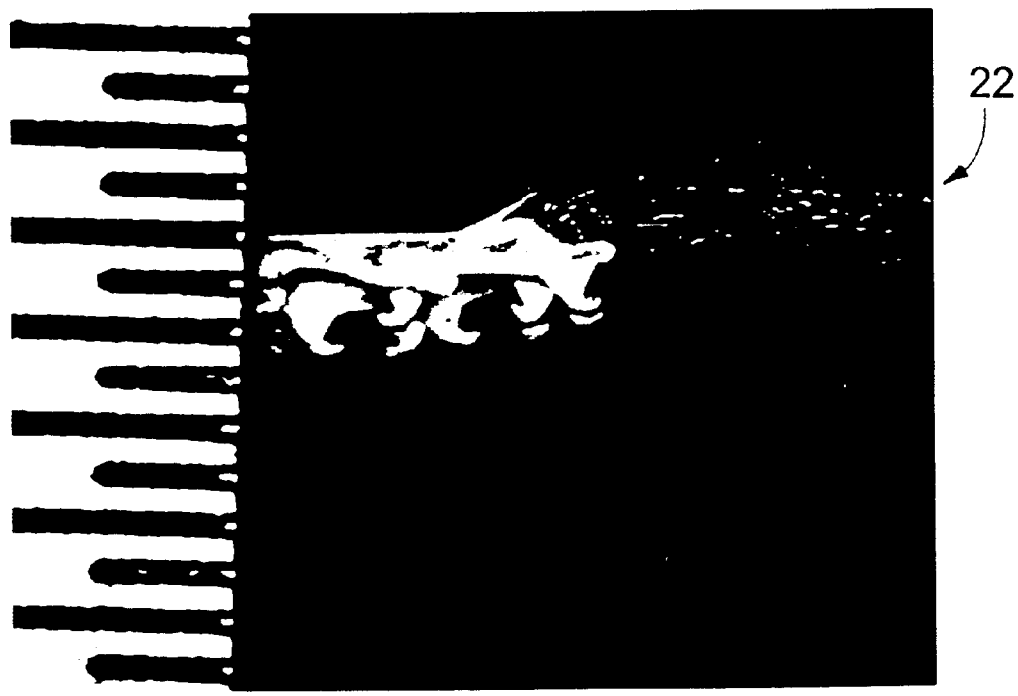
FIG. 5A is an enlarged side view of a hook-and-loop product made by ultrasonically welding a loop product to a hook product.
Figure 5B:
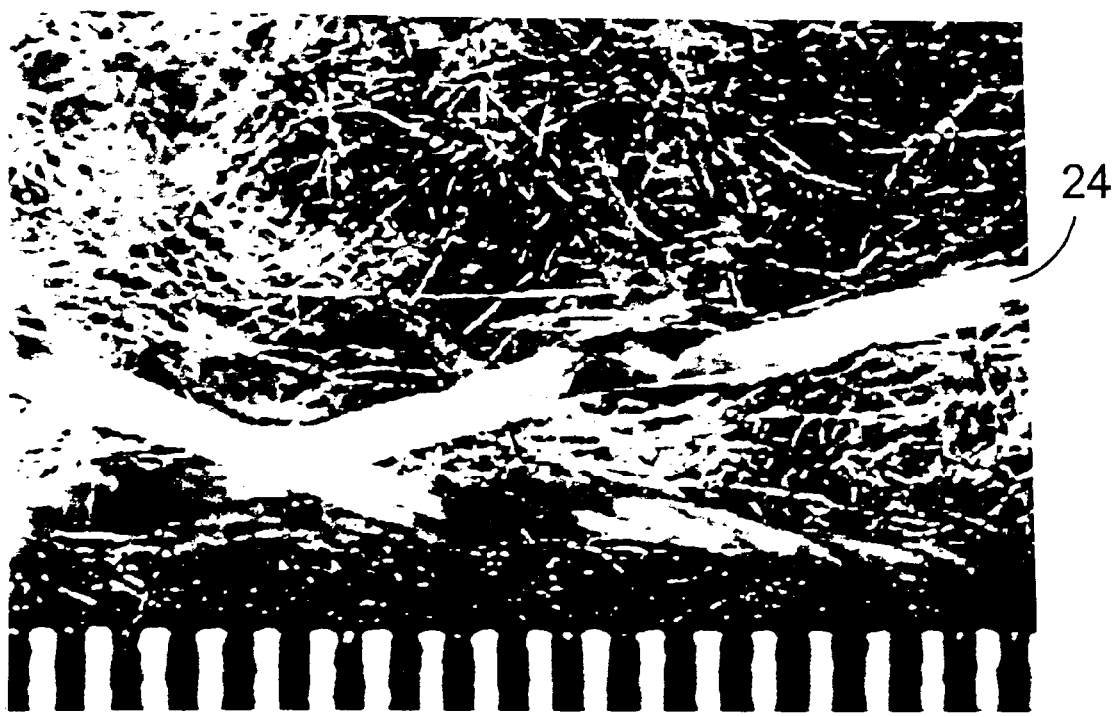
FIG. 5B is an enlarged plan view of a loop product secured by stitching.

The specific loop product 12 of FIGS. 1 and 2 includes about one third by weight water-based acrylic binder produced by mixing 80 parts "NACRYLIC" X-4280, a self-reactive acrylic emulsion, with 20 parts "X-LINK" 2804, a self-crosslinking, polyvinyl acetate/acrylate emulsion, both available from National Starch and Resin Company in Bridgewater, N.J. As produced, loop product 12 substantially consists only of the drawn fibers of the thin mat some of which extend out of the mat to form loops, and the binder. Without any additional backing or laminate, it is strong enough to be handled as a fabric material, and may be applied to surfaces as a closure member by sewing, ultrasonic welding, adhesive, radio frequency welding, or other known attachment means. FIG. 5A, for instance, shows a hook-and-loop product 22 formed by ultrasonically welding a piece of the loop material 12 of FIG. 2 to a piece of CFM-29 hook product. The resulting product 22 can be formed into a closed band by engaging its loops with its hooks. FIG. 5B is an enlarged view of stitching 24 securing the loop product to a substrate.

Figure 6:
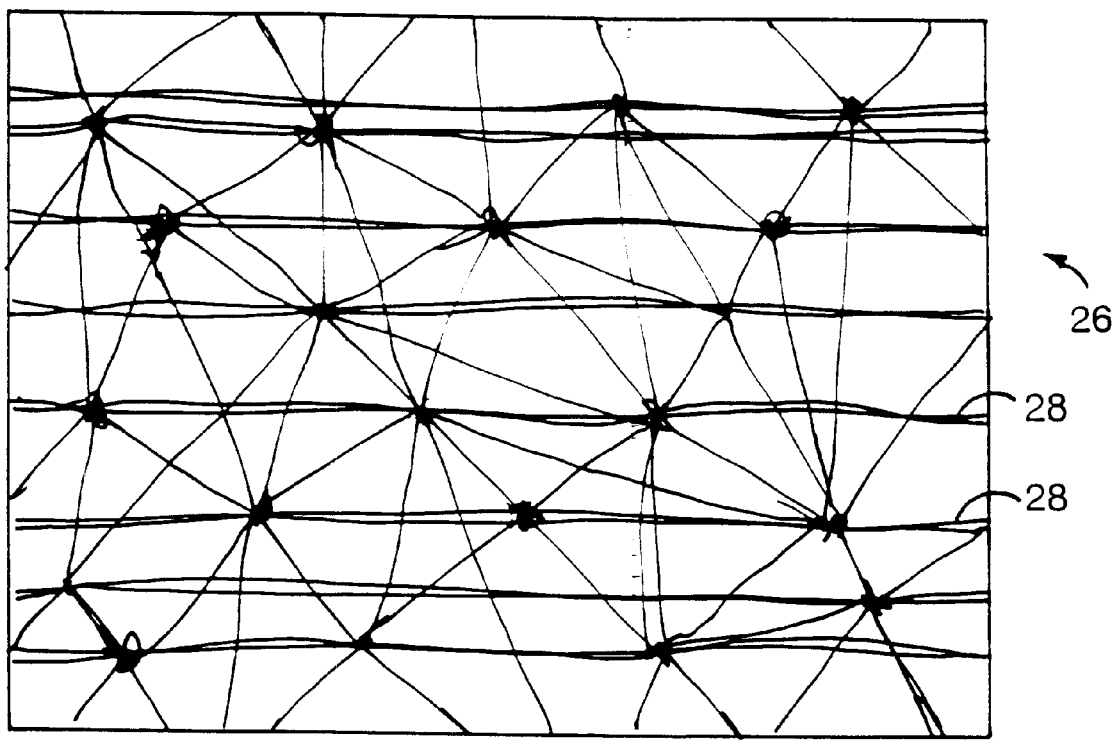
FIG. 6 illustrates a loop material containing longitudinal fibers.

Referring to FIG. 6, another loop fabric material 26 includes, in addition to the drawn, molecularly oriented, randomly laid fibers previously described, continuous robust longitudinal monofilament fibers 28 extending substantially in one direction to augment the tensile strength of the finished fabric in the direction of the strands. For this purpose the diameter of the longitudinal monofilaments is selected to be larger than the barbs of the needles to reduce engagement of the monofilaments by the needles during the needling process. Monofilaments 28 are preferably crimped to enable them to be stretched a limited amount in the machine direction as the fabric is stretched before being stabilized. Alternatively, a stretchable scrim of similarly large fibers or film may be incorporated into the web of fibers to increase tensile strength in both longitudinal and lateral directions.

The very low thickness and stiffness of the above-described loop product, along with its low cost and good closure performance, make it a particularly useful component of many products.

Figure 7A:
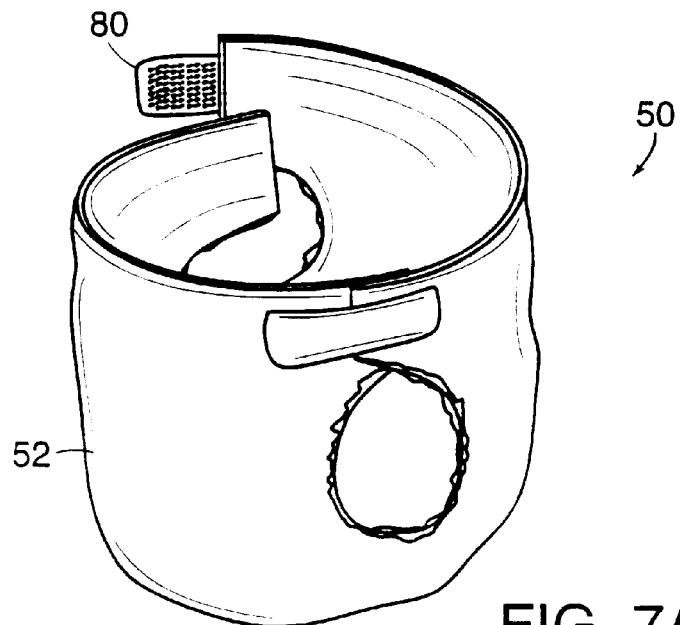
FIGS. 7A–7E depict illustrative products incorporating the loop material of FIG. 2; in order, the illustrated products are; the outer fabric of a disposable diaper (FIG. 7A); a disposable surgical gown (FIG. 7B); a box closure (FIG. 7C), a bag closure (FIG. 7D), and an air filter (FIG. 7E).

Referring to FIG. 7A, a diaper 50 has an outer shell 52 fabricated from the above-described loop product, such that it can be engaged by hooks 80 anywhere over a significant proportion of its surface, while providing the outer "wearing" surface of the article.

In another preferred embodiments, not shown, a panel or patch of the loop product is laminated (directly, or via a carrier sheet,) to the outer liner of a diaper, to provide a suitably large "landing" area that hooks can engage. In one advantageous instance, a panel of the loop product is laminated to a carrier film, which, on its back, has a layer of pressure-sensitive adhesive for automated application to diaper liners or the like during manufacture of the diaper.

Figure 7B:
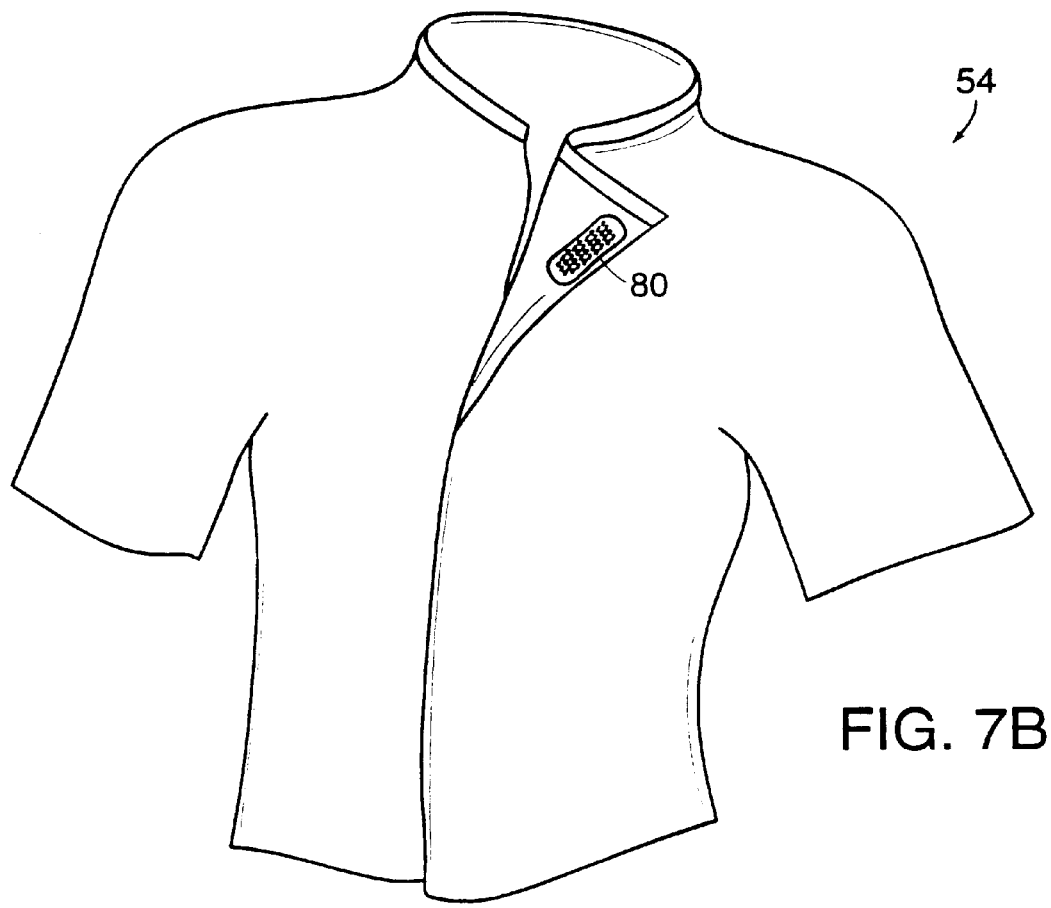

FIG. 7B shows a surgical gown 54 fabricated from the loop material of the invention and capable of being "hooked" by hooks 80 at any point over a large portion of its surface. As with the above-described diaper constructions, as an alternative a panel or patch of the loop product may be attached to the outer surface of a surgical gown.

In such applications in which the products are considered disposable after single use, the loop material only need withstand a relatively small number of hooking cycles (e.g., 3 to 5) over the product's useful life. We refer to these as "low cycle" applications. Loop products in this category may be fabricated by stretching needled fabric in excess of 100%, as much as 150% or more.

Other applications, such as strapping, can require the loop to withstand a higher number of cycles and higher stress. These relatively "high cycle", high strength applications generally are achieved by forming loops with higher denier (or higher tenacity) fibers than those suitable for lower performance conditions. For instance, polyester fibers of 15 denier are advantageously employed for high strength high cycle applications employing large hooks such as CFM 15 (0.035 in. high) or MV 8 (0.100 in. high) or mushroomhook fasteners, all available from Velcro USA Inc. Loop products in this category may be prepared by stretching in the range of 50 percent to 100 percent stretch.

Figure 7C:
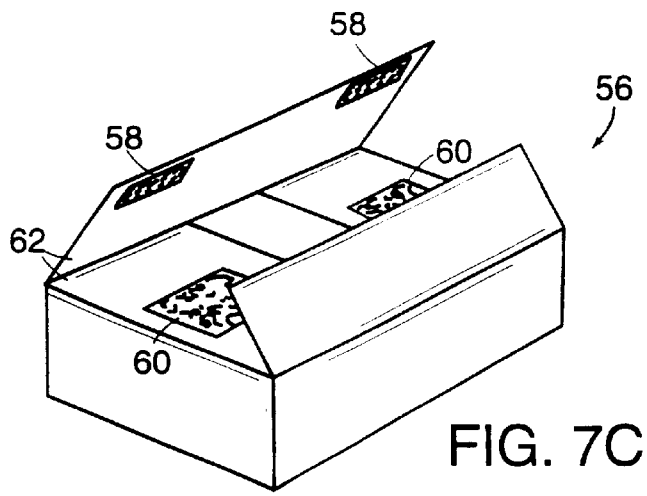

FIG. 7C shows a box 56 with hook closure strips 58 that engage loop closure strips 60 of our loop product to hold the flaps 62 of the box in a closed position. Loop closure strips 60 have pressure sensitive adhesive backing, by which they are permanently applied to box flaps 62. Supplied as die cut sections on a release liner, loop strips 60 can be applied to the box flaps with a common, automatic label head, for instance. The box is useful for applications where it must be repeatedly opened while its contents are progressively consumed, for example a pet food box.

There are many different adhesives and backing materials that can be included on the back (i.e., "non-loop") side of the loop product, either in place of or in addition to the binder described above. For instance, a binder adhesive may be formulated to be pressure sensitive, with or without a release liner, such that the final product may be applied to a substrate by the application of pressure. Without a release liner, as the product is rolled or spooled the pressure sensitive backing lies against and adheres to the hook-engageable loops to keep the product in rolled form until unrolled by peeling, leaving a sufficient amount of undisturbed adhesive on the back of the fabric to secure the product to a substrate. Other coatings, such as heat sensitive or "hot-melt" coatings, or water-activated or solvent-activated coatings, may also be used with suitable heating or application of activating fluid at the time of activation to secure the loop material to the item on which a closure is desired.

Figure 7D:
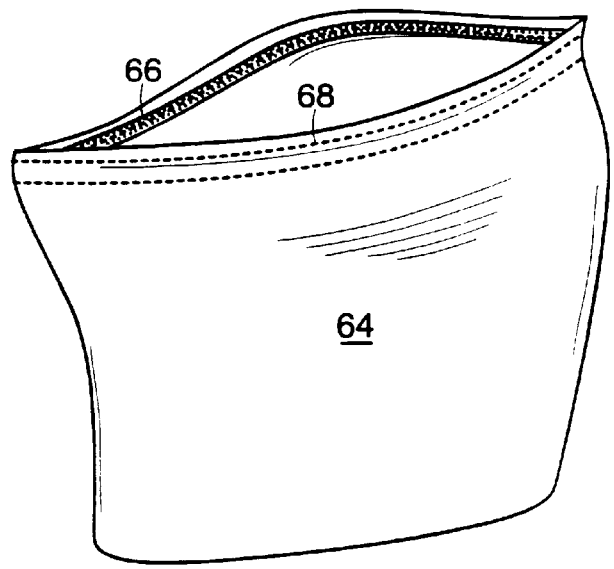

In cases where the fiber material is chosen to be of the same type as, or compatible with, a substrate material upon which it is desired to secure the loop fabric, the loop product may be directly thermally fused to the substrate. For instance, FIG. 7D shows a polyethylene bag 64 to which a polyethylene hook strip 66 and a polyethylene loop strip 68 have been thermally bonded or welded. It can be closed in rapid fashion by simply pressing one end of the closure together by opposed fingers and sliding the fingers from one end to the other of the closure. Such a closure does not require accurate alignment of the mating features to be secured, and can enable some desirable venting and filtration through the secured closure. Such a venting, filtering closure, which is practically enabled by the low cost of the loop product of the invention, is useful for vegetable containers and charcoal briquette bags, for instance. The closure also allows equilibration of the pressure inside and outside of bags or packages constructed to travel in airplane cargo holds.

The loop product may be flame-laminated to other materials, such as to open-cell foam. The flame lamination process not only adheres the loop product to the foam, but stabilizes the foam. Products economically produced in this manner include disposable medical devices, such as limb or joint braces, straps for colostomy bags, and blood pressure cuffs. Other products include merchandise and trade show displays with large surfaces of loop product upon which hooks can be used for mounting various displays.

Figure 7E:
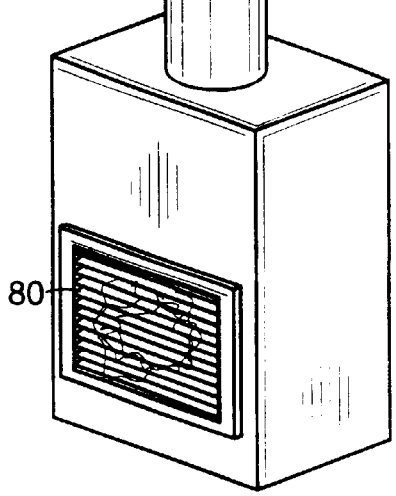

The low density of the loop material is constructed and arranged as a filter media for filtering relatively high volume flows of air, such as in HVAC systems and the like. FIG. 7E shows the loop material described above, associated with a suitable frame as an inexpensive, replaceable filter 80. Stiffened by suitable proportions of binder and/or a stiffening agent applied to the web, the loop material is preferably permanently corrugated to increase the surface area of the filter intercepting a flow of air and to enhance the rigidity of the filter.

Figure 8:
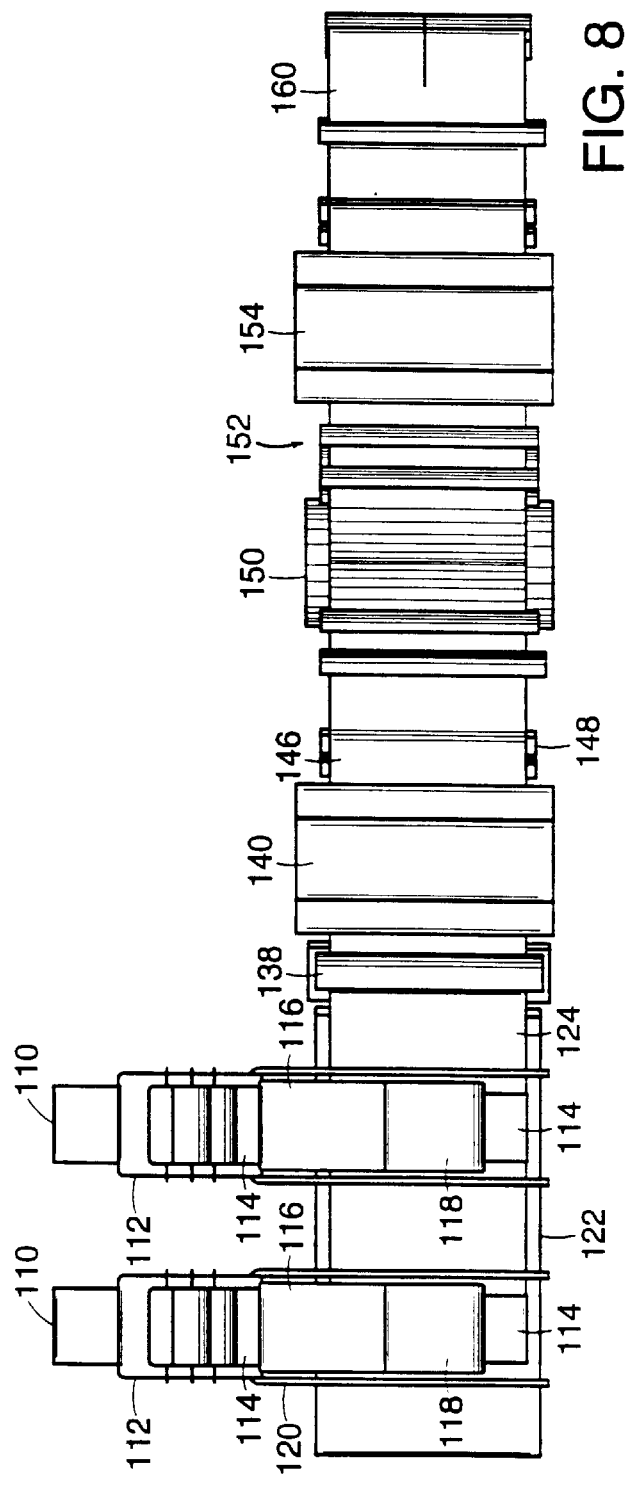
FIG. 8 is a top view of an apparatus for making a nonwoven fabric.
Figure 9:
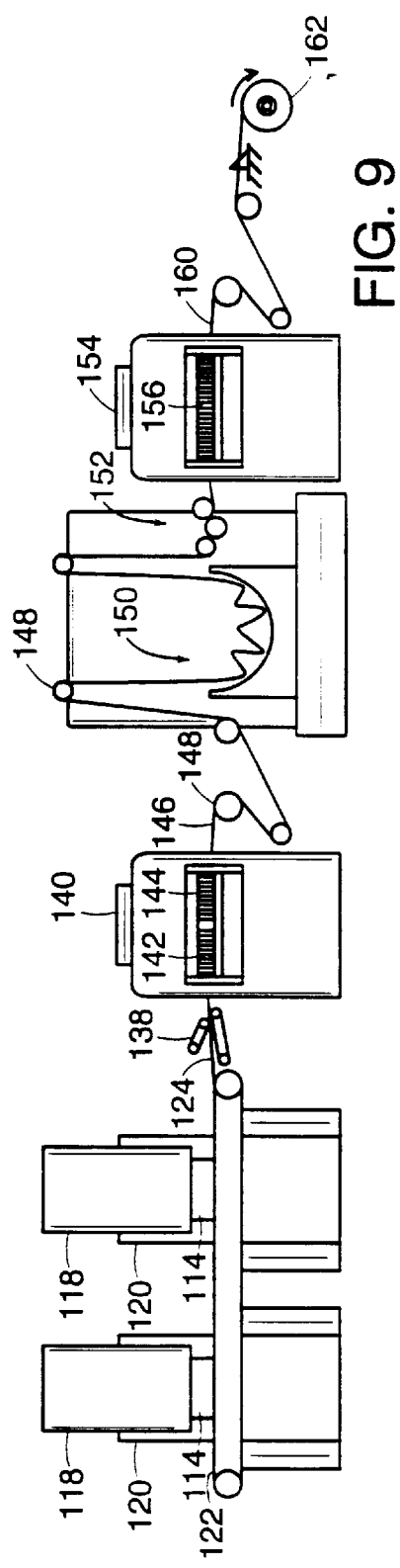
FIG. 9 is a side elevational view of the apparatus of FIG. 8.

Referring to FIGS. 8 and 9, an example of apparatus for producing our loop product includes a feeder 110 (with, e.g., bale breakers, blender boxes or feed boxes), which feeds staple fibers of a desired length of drawn fibers to carding machines 112. The carding machines 112 card the staple fibers to produce carded webs of fibers 114 which are picked up by the take-off aprons 116 of crosslappers 120. The cross-lappers 120 also have lapper aprons 118 which traverse a floor apron 122 in a reciprocating motion. The cross-lappers lay carded webs 114 (of, e.g., about 12 to 18 inches width and about one inch thickness) on the floor apron 122 to build up several thicknesses of criss-crossed web to form a batt 124 (of, e.g., about 90 to 120 inches in width and about four inches in thickness). In preparation for needling, batt 124 is gradually compressed in a tapered nip between floor apron 122 and a moving overhead apron 138 to reduce its thickness to about one inch. A relatively thin, low density batt can thus be produced.

Needling of batt 124 is performed in multiple, sequential needling stages in order to provide a very high density of needle penetrations without destroying the low density batt. In the presently preferred method felting needles are employed having fiber-engaging barbs on their sides.

From floor apron 122, the batt is passed to a first needle loom 140 with two needling stations 142 and 144 having rows of notched (i.e., barbed) needles. Needling station 142 needles the batt of staple fibers from its upper surface at a density in the range of 100 to 160 punches per square inch (in this example, 134 punches per square inch), Subsequently, needling station 144 needles the once-needled batt a second time, with needles which penetrate the batt from its upper surface at a density in the range of 500 to 900 punches per square inch (in this example, 716 punches per square inch) to produce a needled batt 146. We refer to the operation of loom 140 as the first needling stage. Additional information on needling processes can be obtained from the Association of the Nonwoven Fabrics Industry (INDA) of Cary, N.C., which publishes the *INDA Nonwovens Handbook*.

After the first needling stage, needled batt 146 is passed between drive rolls 148 and into a J-box accumulator 150 which, besides holding a bank of batt to accommodate variations in processing rates, allows the needled batt to relax and cool before entering the second needling stage. Alternatively, the needled batt 146 may be spooled after the first needling stage, with subsequent operations performed on a second line. If materials and conditions allow, the needled batt may be passed directly from the first needling stage to the second needling stage without accumulation, but care should be taken to ensure that the batt is sufficiently cool and relaxed to withstand the second needling stage.

From J-box accumulator 150, needled batt 146 is pulled through a guider/spreader 152 (of, e.g., the one-over-two configuration) to properly apply light tension to the batt as is customary for needling, without significant stretching of the batt. It then passes through a second needle loom 154 for a second needling stage. The operation of this second stage is referred to "super needling", as it is a very dense secondary needling operation and produces many loops of substantial loft. Loom 154 has a single needling station 156 in which needled batt 146 is needled from the lower side to produce high-loft loops extending from the upper side. To produce such loops, the sharp tips of the notched needles of loom 154 are extended a substantial distance (e.g., about one-fourth of an inch) beyond the thickness of the batt in the same direction as the needles of needling station 142, pushing individual fibers away from the bulk of the batt to form upstanding loops. When the needles retract, the loops remain.

This super-needling process does not require special needling bedplates or supporting brushes into which the needles extend, such as are employed in structured or random velour looms, although such techniques may be employed to advantage, e.g., where large loops are desired for use with large hooks. The super-needling is primarily characterized as an extremely dense needling, on the order of about 1000 to 2000 punches per square inch (in this example, about 1400 punches per square inch). Standard barbed needles are employed, such as triangular section 15×18×42×3 C222 G3017 felting needles from Groz-Beckert. During this secondary needling operation, individual fibers of the batt are pushed through the loop side of the batt to produce loose, relatively lofty loops. Together, these loops give the loop side of the super-needled batt a fuzzy appearance and feel. Too much extension of the individual loop fibers at this point can cause them to break during subsequent stretching, so the distance the needles extend through the batt is selected in consideration of the denier and tenacity of the fibers used. We have found that extending the needles about one-fourth of an inch beyond the batt works well for 6 denier fibers with a tenacity of about 3.5 grams per denier.

Figure 10:
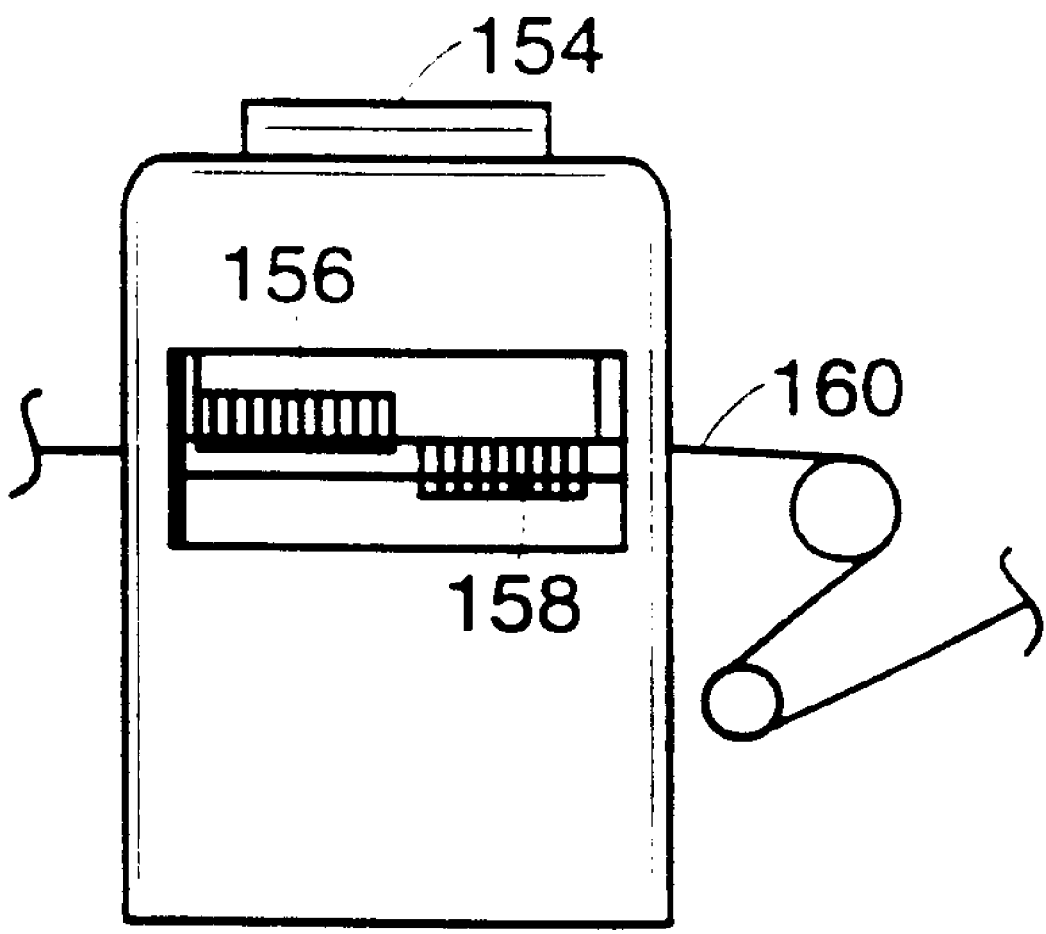
FIG. 10 shows an alternative arrangement of the second needling stage of the apparatus of FIG. 9.

In one embodiment, illustrated in FIG. 10, needle loom 154 has an additional, second needling station 158. After producing high-loft loops extending from one surface, the batt is super needled in the other direction to produce loops extending from its other surface, such that both sides have extended loops.

After leaving loom 154, the super-needled batt 160 is split into two running 45 inch widths and spooled on rolls 162. As shown in FIG. 11, the fibers of batt 160 have been entangled by the needle punching process to create loose entanglements throughout the batt. At this stage, the batt is not an acceptable loop product for many hook-and-loop fastening applications, as the individual loops may be relatively easily pulled away from the batt and are not well anchored at the entanglements.

After super-needling, the loop definition, see FIG. 11A, on the working side of the batt is not as distinct as it can be after the stretching that is employed to produce products with loop trees and bushes, compare FIGS. 11, 11A with FIGS. 2 and 3.

The batt following super needling has a fair amount of loft and resiliency, with the loops and other fibers of the batt forming loose, gentle arches between entanglements. At this point the batt is very flexible, and the density of fibers gradually decreases away from either side of the material. At first glance, it can be difficult to tell which side has been super-needled, if only one side has been subjected to that action. Batt 160, in this example, has an overall thickness, including loops, of about ³⁄₁₆ inch and a weight of between about 2 and 4 ounces per square yard.

Figure 12:
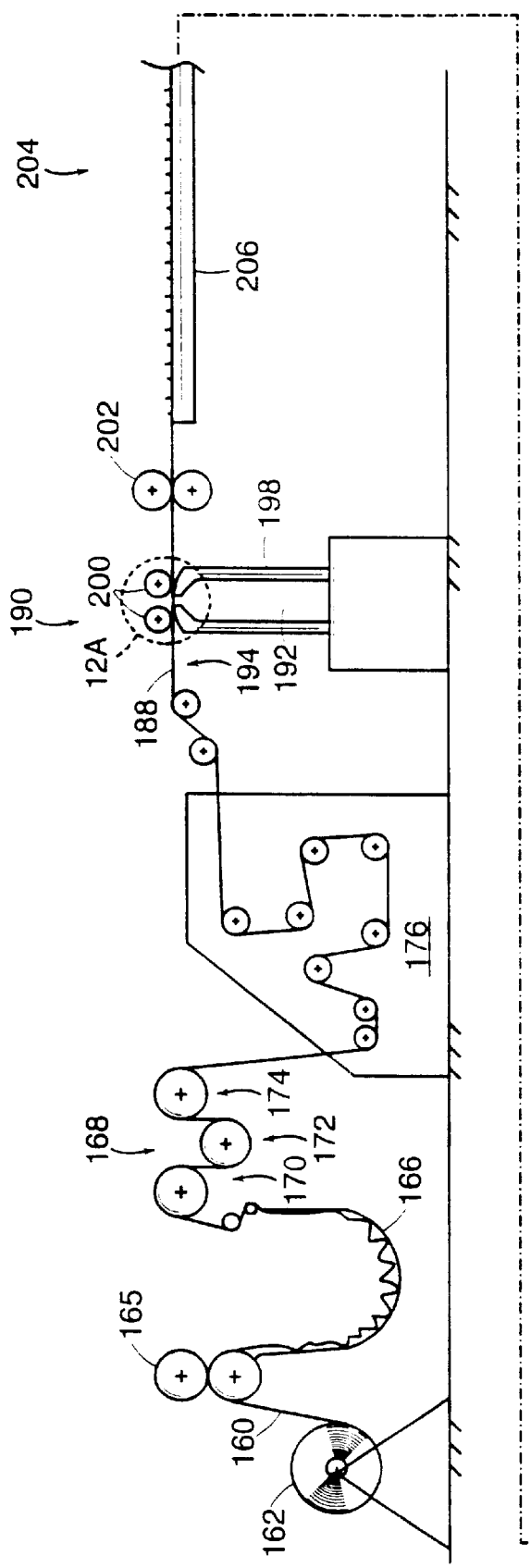
FIG. 12 is a schematic view of an apparatus for stretching and stabilizing a non-woven material.
Figure 12:
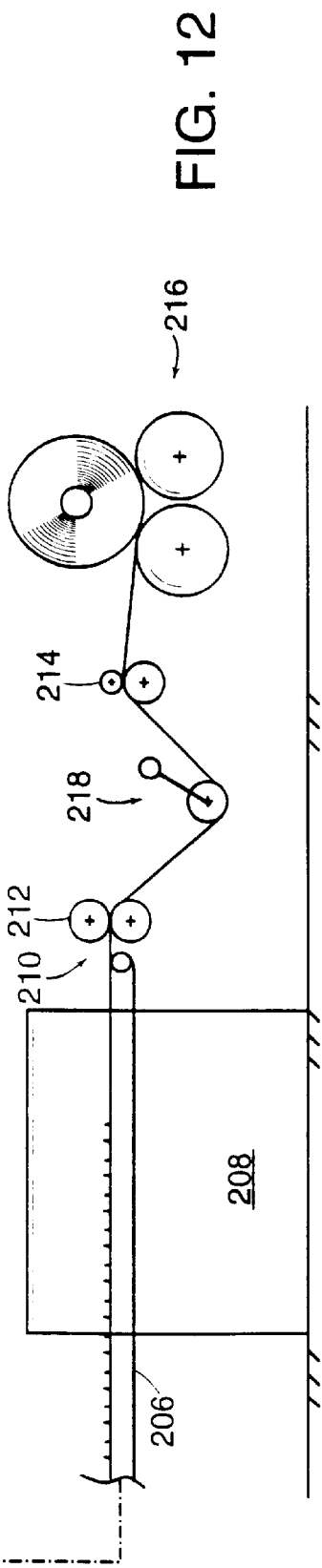

Referring to FIG. 12, a spooled length of super-needled batt 160 is spooled from roll 162 by drive rolls 165 and into a J-box accumulator 166, allowing roll 162 to be replaced and the batt spliced without interrupting further processes. The J-box also allows the batt to recover from any elastic deformation caused by the spooling process. Batt 160 is pulled from accumulator 166 through a guider 168 to center the batt in the cross-machine direction. Guider 168 includes three rolls in a two-over-one configuration. The first and second rolls 170 and 172 have left and right herringbone pattern scroll surfaces originating at the center of the roll that, being slightly overdriven, urge any wrinkles in the batt toward its edges to remove them. The third roll, roll 174, is a split braking roll to controllably tension either half of the batt to guide the fabric to the left or right as desired.

From guider 168 the batt passes through a tension controller 176 that maintains a desired tension in the batt through the subsequent binder application process. Controlling the difference between the speed of tension controller 176 and downstream drive rolls 202 applies a desired amount of machine direction stretch to the batt prior to cross-machine stretching. In some cases, no substantial machine direction stretch is purposefully applied, any noted machine direction lengthening being due only to minimal web processing tension in the supply batt. In other cases, machine direction stretch is purposefully induced by running drive rolls 202 faster than tension controller 176.

Figure 12B:
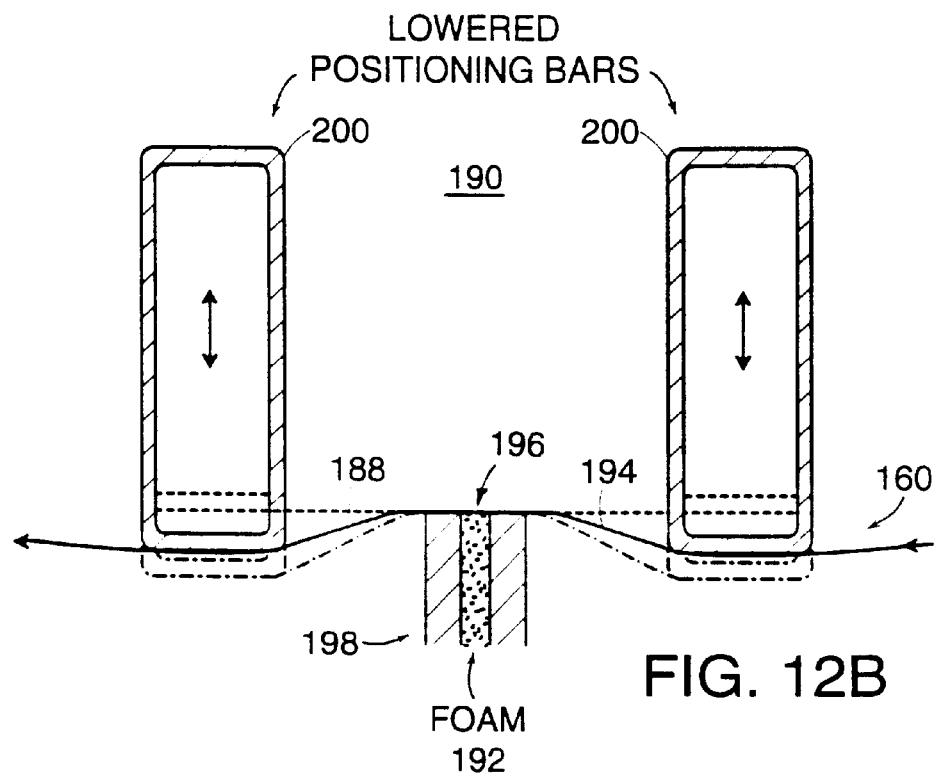
FIG. 12A and 12B are enlarged views of area 12A in FIG. 12 under two different conditions of operation.
Figure 12A:
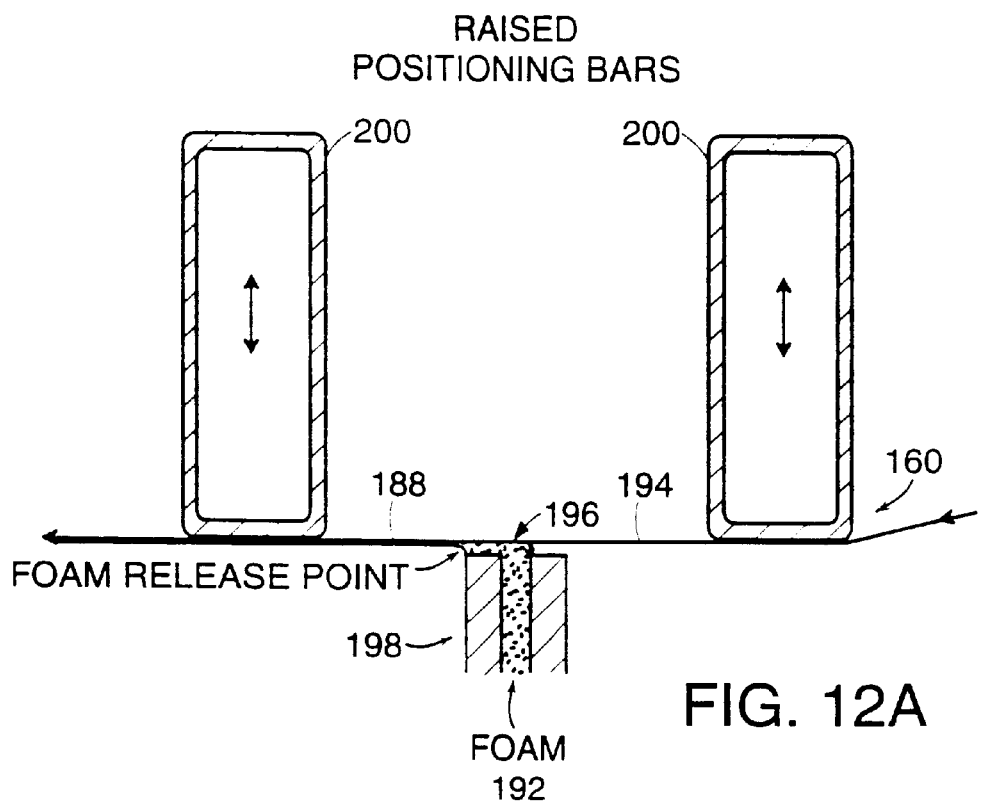

In the embodiment in which batt 160 has been super-needled to produce loops extending from only its front side 188, batt 160 is next passed through a coating station 190, see FIGS. 12a and 12b that illustrates the range of adjustment, in which a foamed, water-based adhesive 192 (i.e., a water-based adhesive, whipped to entrain air) is applied to the back side 194 of the batt across its width. The foamed liquid adhesive is pumped at a controlled rate through a long, narrow aperture 196 in the upper, surface of the applicator 198 as the batt is wiped across the aperture, thereby causing the adhesive to partially penetrate the thickness of the batt. Positioning bars 200, on either side of aperture 196, are raised and lowered to control the amount of pressure between batt 160 and applicator 198. The depth of penetration of the adhesive into the batt is controlled (e.g., by the flow rate and consistency of adhesive 192, the speed of batt 160 and the position of bars 200) to sufficiently coat or penetrate enough of the fiber entanglements to hold the product in its final form, while avoiding the application of adhesive 192 to the loop-forming fiber portions of the front side 188 of the batt. The foaming of the liquid adhesive before application helps to produce an even coating of the back side of the batt and helps to limit penetration of the fluid adhesive into the batt. After the semi-stable foam is applied it has a consistency similar to heavy cream, but the bubbles quickly burst to leave a liquid coating that flows as a result of wetting and surface tension, into the tightening fiber entanglements. Alternatively, the foam may have a thicker consistency, more like shaving cream, to further reduce the penetration into the batt and form more of a distinct resinous backing. A non-collapsible (i.e., stable) foam of urethane or acrylic, for instance, is useful to produce a radio frequency-weldable backing which functions as a water barrier. Such a product has particular application to disposable garments and diapers.

It is important that the binder (e.g., adhesive 192) not interfere with the loop-forming portions of the fibers on the front side 188 of the batt. It is not necessary that the knot bases be completely covered by binder; it is sufficient that they be secured by the binder in the finished product to stabilize the fabric against significant further stretching and to strengthen the bases of the loops. Preferably, the binder is at least partially in liquid form to wick into the entanglements before and while they are subsequently tightened during stretching.

After leaving coating station 190, the material is subjected to stretching in the plane of the web. In the presently preferred case the web is wound through variable speed drive rolls 202 and onto a tenter frame 204 for cross-machine stretching (i.e., stretching in the cross-machine direction). The speed of drive rolls 202 is adjustable, with respect to both tension control 176 and the rails 206 of the tenter frame, to cause a predetermined amount of machine direction stretch in the batt, either between tension control 176 and drive rolls 202, or between drive rolls 202 and frame rails 206, or both. In some embodiments no permanent machine direction stretch is applied, but the batt is nevertheless held in tension to control adhesive penetration and maintain proper frame rail pin spacing. In other embodiments the batt is generally stretched, in total, between about 20 percent and 50 percent in the machine direction before tentering.

As it enters tenter frame 204, the 45 inch wide batt 160 is engaged along its edges by pins of frame rails 206 that maintain the machine-direction dimension of the material as it is stretched in the cross-machine direction. The spacing (of, e.g., about 3/16 inch) between adjacent pins is maintained throughout the length of the tenter frame, such that no additional machine-direction stretch is applied. Due to the needling, batt 160 should have enough tensile strength to be properly engaged by the rail pins and withstand the subsequent cross-machine stretching.

Figure 13:
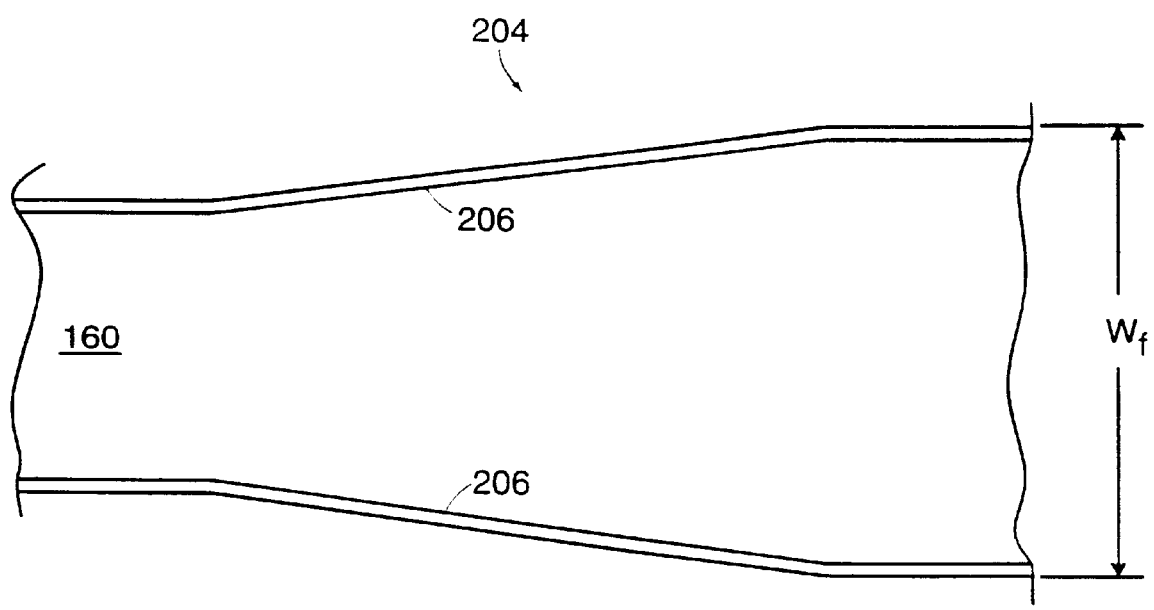
FIG. 13 is a top view of the tenter frame of FIG. 12.

As shown in FIG. 13, tenter frame 204 has a tapered section where the rails 206 separate at a constant, adjustable range rate over a machine-direction length of about 10 feet to a final width $w_f$, $w_f$ can range from 45 to about 65 to 69 inches. This equates to a cross-machine stretch, in this particular embodiment, of about 50 percent. In general, to take advantage of the economics that can be realized according to the invention, the batt should be stretched to increase its area by at least about 20 percent (we call this "percent areal stretch"), preferably more than about 60 percent areal stretch and more preferably more than about 100 percent areal stretch, to increase the area of the product while tightening the binder-containing entanglements of the batt that contribute to improvement in the strength of anchorage of the individual loops. We have found that in some cases the super-needled batt can be stretched, by employing the above method, at least 130 areal percent or more and provide very useful hook-engaging properties. The more the stretch, the greater the overall yield and the lighter in weight the final product. Even greater overall cross-machine stretch percentages can be employed, for instance by using multiple tentering stages in situations wherein the batt is constructed to withstand the stretch and still be able to reasonably engage hooks. In one instance, the super-needled batt described above was stretched from an initial width of 45 inches to 65 inches, softened (by adding a softener), slit to a 45 inch width, stretched a second time to 65 inches width before applying a binder, and still had useful, hook-engageable loops. In some cases final product widths of 6 to 8 feet or even much more can be achieved.

It is believed that the "loop trees" (see FIG. 3B), which do not distinctly appear in the pre-stretched batt, obtain their final form as fibers of the ground portion of the web are pulled and the entanglements beneath them are tightened during stretching to form knots. As the batt is stretched, the tension in the taut fibers of the web forces some of the loop trees to stand erect, such that the overall thickness of the stretched batt can actually be greater than the unstretched batt. To extend the horticultural analogy, the homogeneous thicket of the loop surface of the unstretched batt becomes the orchard of spaced clusters of the stretched product.

Despite the relatively wide loop spacing that is achieved, the loops, after curing of the binder, are found to be so strongly anchored and so available for engagement by the hooks, that a web unusually treated according to these techniques can perform in an excellent manner despite having a gossamer appearance.

Referring back to FIG. 12, while the stretched batt is held on frame rails 206 in its stretched condition it is passed through an oven 208 in which the product is heated to dry and cross-link acrylic binder 192 and stabilize the dimensional integrity of the batt. Oven 208 is essentially a convection drier with air venturi nozzles which blow hot air up into and down onto the web to evaporate some of the water of the adhesive. In this example, the heating time and temperature are about one minute and 375 degrees F., respectively. In some embodiments (not shown), the batt is retained on frame rails 206 for secondary coating passes through additional coating stations and drying ovens, thereby building up a desired laminate structure for particular applications.

In another embodiment, hook-engageable loops are formed on both sides of the web by needling, by the superneedling techniques acting on staple fibers that have been described, or by other known techniques. After forming the loops the web is passed through a bath of binder. In some cases, where the loops are relatively stiff and the binder is of suitably low viscosity, after removal from the bath the binder drains from the loops and the loops, by their own resiliency and stiffness resume their free-standing stance while capillary action retain the binder in the center of the fabric. The web is then subjected to stretching and curing as above.

In other instances, as where the loop material is less stiff, auxiliary means are employed to remove excess binder after passing through the bath, as by passing the fabric through a nip of squeeze rolls, or by subjecting both sides of the fabric to an air knife, or by blotting followed, in each case for instance by blowing air or otherwise loosening the loops and causing them to stand upright.

Other embodiments carrying hook-engageable loops on one or both sides, and incorporating heat-fusible binder fibers or other heat-fusible binding constituents, are bonded by non contact means such as by blasts of hot air directed at both sides of the fabric at temperatures sufficient to melt the heat-fusible binding material and lock the fabric structure in its stretched condition.

In another instance, heat fusible fibers or other material colored black or otherwise adapted to absorb radiant heat, are activated by radiant heaters to bind the ground portion of the fabric following stretching.

Figure 12C:
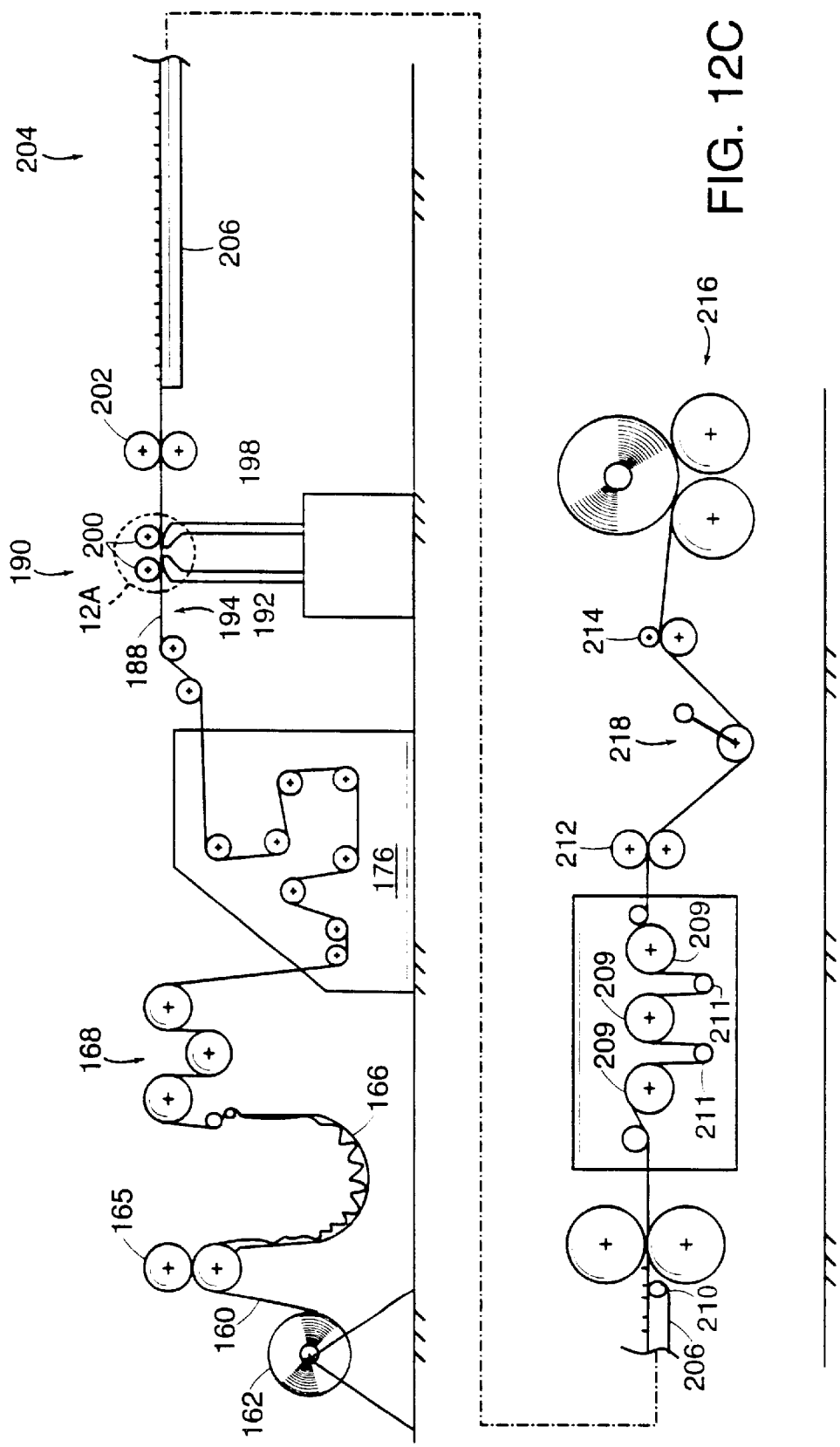
FIG. 12C illustrates another embodiment in which the product is stabilized by fusing fibers.

Referring to FIG. 12C, an alternative embodiment employs heated rolls 209 ("hot cans") or platens to stabilize the back side of the fabric while it is stretched in the cross-machine direction. This embodiment does not require a coating or adhesive when using thermoplastic fibers, as the fibers are locally fused together by heat. Cooled rolls 211 engage the loop side of the fabric during passage, to prevent damage to the hook-engageable loops.

The batt exits oven 208 still attached to the pins, and is then pulled from the pins by a de-pinning device 210 and a pair of drive rolls 212. The finished wide batt is then slit, if desired, into appropriate multiple widths by a slitter 214 and spooled on a driven surface winder 216. A dancer 218 between drive rolls 212 and slitter 214 monitors the tension in the batt to control the speed of winder 216. Slitter 214 can also be used to trim off the edges of the batt that include the material outboard of the frame rails through the tenter frame. Optionally, the finished batt can be brushed before or after spooling to disentangle loosely-held loop fibers to improve the consistency of the closure performance between the first and subsequent engagements with a hook product.

In order to produce the product of FIG. 6, the longitudinal continuous fiber strands 28 are added to the batt prior to needle punching. These fibers are preferably crimped enough to allow the fibers to retain their integrity after the needle-punching process, to be stretched a limited amount in the machine direction as the batt is stretched.

In another embodiment, an unstretched batt 160 (FIG. 11) is not purposefully stretched after the application of the binder. Instead, the batt is stabilized at substantially the same width and entanglement density it had as it left the needling looms as the binder cures. The final, unstretched product is spooled without compression nipping, in order to avoid compressing the upstanding loops.

It will be understood that the novel stretching technique to tighten fiber entanglements of a hook-engageable loop-defining non-woven fabric to provide stronger anchorage-loops or improve the presentation of the loops, or to increase yield, can be employed to advantage on other stretchable, loop forming non woven webs. Thus, in its broadest aspects, the invention is not to be limited to use of needled webs. Webs formed by hydro or air current entanglement can for instance thus be employed, etc.

In most cases where significant strength performance is desired, it is preferable to employ non-woven staring materials formed of staple fibers to take advantage of their drawn, molecular oriented structure, or other fibers of the substantial tenacity.

Other features and advantages of the invention will be realized, and are within the scope of the following claims.

What is claimed is:

1. A method of forming a fastener product having loops at an exposed front surface for hook-and-loop fastening, employing as a starting material a nonwoven web of fibers of substantial tenacity that are capable of forming said loops, the web having a front and back surface, the steps of:
   stretching the nonwoven web at least 10 percent in a first direction of extent of the nonwoven web,
   stretching the nonwoven web at least 10 percent in a second direction of extent of the nonwoven web, the second direction lying substantially perpendicular to the first direction so that the nonwoven web is in a state of being stretched at least 10 percent in each of two directions, and
   stabilizing the web in its said stretched state under conditions in which loops formed by said fibers of said nonwoven material are exposed in hook-engageable position at least at said front surface.

2. The method of claim 1 in which the form of the loops of fibers and their distribution are at least partially determined by said stretching in two directions.

3. The method of claim 1 in which the nonwoven web is in a stretched state of at least 25% in each of said two perpendicular directions when it is stabilized.

4. The method of claim 1 in which the nonwoven web is in a state of at least 75% areal stretch when it is stabilized.

5. The method of claim 4 in which said state is at least 100% areal stretch.

6. The method of claim 1 in which stretching in one of said directions is produced in machine direction by tension on a continuous length of said nonwoven web, said machine direction stretching being about 50%.

7. The method of claim 1 in which stretching in one of said directions is produced in machine direction by tension on a continuous length of said nonwoven web produced by a drive roll engaged with the web advancing substantially faster than an upstream tension-controlling roll engaged with the web.

8. The method of claim 1 in which stretching in one of said directions is produced on a continuous length of said nonwoven web in a cross machine direction, said cross machine direction stretching being about 50% or more.

9. The method of claim 1 in which stretching in one of said directions is produced on a continuous length of said nonwoven web in a cross machine direction by a tenter frame.

10. The method of claim 9 in which said tenter frame passes through an oven.

11. The method of claim 1 in which said nonwoven web is a needled web of fibers.

12. The method of claim 1 in which said nonwoven web is a hydroentangled web of fibers.

13. The method of claim 1 in which said nonwoven web is a web formed by air current entanglement of fibers.

14. The method of claim 1 in which said nonwoven web is at least partially stabilized in said stretched state by applying material to the back surface of said web.

15. The method of claim 14 in which the material applied is a fluid binder material which subsequently is solidified.

16. The method of claim 1 in which said nonwoven web is at least partially stabilized in said stretched state by solidification of at least partially melted fibers of low-melt polymer.

17. The method of claim 1 in which binder material at the back surface of said nonwoven web is formed as a backing.

18. The method of claim 1 in which binder material at the back surface of said nonwoven web is formed as an impermeable barrier.

19. The method of claim 1 in which said barrier is a water barrier.

20. The method of claim 1 including applying a binder comprised of fire-retardant material.

21. The method of claim 1 in which a layer is adhered to the back surface of said nonwoven web.

22. The method of claim 21 in which said layer is a supporting fabric.

23. The method of claim 1 in which the back surface of said nonwoven web is laminated to a carrier layer.

24. The method of claim 23 in which said carrier layer is a film.

25. The method of claim 1 including laminating said nonwoven web to one side of a carrier layer, and providing on the opposite side of said carrier layer a layer of pressure-sensitive adhesive for application of the resulting assemblage to a surface.

26. The method of claim 25 including forming from the resulting lamination a panel adapted for application to a wearable article to provide a landing area where hooks can engage.

27. The method of claim 26 in which said panel is sized to provide a landing area on a diaper liner.

28. The method of claim 26 in which said panel is sized for application to a gown.

29. A method of forming a loop product for a hook-and-loop fastener, the method comprising the steps of entangling fibers to produce a non-woven fabric of fibers joined at entanglements, with loops of some of the fibers extending from at least one side of the fabric;

subsequently stretching the fabric at least 10 percent in each of two perpendicular directions to tighten the entanglements to form knots, and binding the knots to hold the fabric in its thus stretched state.

30. A method of forming a loop product for a hook-and-loop fastener, the method comprising the steps of forming a batt of loose, staple fibers;

forcing some of said fibers through the batt, thereby entangling the fibers to produce a non-woven fabric of fibers joined at entanglements, and also thereby forming fibrous loops extending from one side of the fabric;

coating at least some of the entanglements of the fabric with a fluid binder; and subsequently stretching the fabric at least 10 percent in each of two perpendicular directions to tighten the entanglements to form knots, the binder, upon solidifying, adapted to hold the fabric in its stretched state.

31. The method of claim 29 or 30 wherein the fibers are entangled by through-punching with needles.

32. The method of claim 31 wherein, for entangling the fibers needling a layer comprised of fibers a first time with a needle-punching density of at least 100 punches per square inch, and needling a subsequent time with a greater needle-punching density.

33. The method of claim 32 wherein the needling a subsequent time is with a needle-punching density of between about 1200 and 1600 punches per square inch.

34. The method of claim 31 wherein the needling a first time is conducted in a first direction, and needling said subsequent time is conducted in a second direction, the second direction opposite to the first direction.

35. The method of claim 29 or 30 further comprising setting a binder applied to the fabric to stiffen the knots of the stretched fabric.

36. The method of claim 29 or 30 wherein the fabric is stretched by at least 15 percent in a cross-machine direction.

37. The method of claim 29 or 30 wherein the fabric is stretched to increase its area by at least about 50 percent.

38. The method of claim 37 wherein the fabric is stretched to increase its area by at least about 100 percent.

39. The method of claim 29 or 30 further comprising the step of brushing said loops to disentangle loosely-held loop fibers.

40. A method of forming a loop component of a hook and loop fastener comprising forming a stretchable non-woven fabric comprised of entangled fibers, some of the fibers forming hook-engageable loops that extend from entanglements, thereafter stretching the thus formed fabric at least 10 percent each in two perpendicular directions thereby tightening at least some of the entanglements into knots, and, while said fabric remains in said thus stretch state, binding the stretched fabric to give it stability.

* * * * *

UNITED STATES PATENT AND TRADEMARK OFFICE
CERTIFICATE OF CORRECTION

PATENT NO. : 6,598,276 B2
DATED : July 29, 2003
INVENTOR(S) : William H. Shepard and Paul R. Erickson It is certified that error appears in the above-identified patent and that said Letters Patent is hereby corrected as shown below:

<u>Column 19,</u>
Line 6, replace "claim 1" with -- claim 18 --.

Signed and Sealed this

Sixth Day of April, 2004

JON W. DUDAS
*Acting Director of the United States Patent and Trademark Office*